US005922780A

United States Patent [19]

Dyer et al.

[11] Patent Number: 5,922,780
[45] Date of Patent: Jul. 13, 1999

[54] CROSSLINKED POLYMERS MADE FROM 1, 3,7-OCTATRIENE AND LIKE CONJUGATED POLYENES

[75] Inventors: John Collins Dyer; Bryn Hird, both of Cincinnati, Ohio; Pui Kwan Wong; Sharon Marie Beshouri, both of Houston, Tex.

[73] Assignee: The Procter & Gamble Company, Cincinnati, Ohio

[21] Appl. No.: 08/370,691

[22] Filed: Jan. 10, 1995

[51] Int. Cl.⁶ .................................. C08F 36/00; C08J 9/28
[52] U.S. Cl. ..................... 521/150; 521/64; 521/84.1; 521/109.1; 521/149; 526/335; 526/340.3
[58] Field of Search .................... 521/64, 84.1, 109.1, 521/149, 150; 526/335, 340.3

[56] References Cited

U.S. PATENT DOCUMENTS

| | | |
|---|---|---|
| 3,255,127 | 6/1966 | Bonin et al. . |
| 3,256,219 | 6/1966 | Will . |
| 3,431,911 | 3/1969 | Meisel . |
| 3,563,243 | 2/1971 | Lindquist . |
| 3,565,817 | 2/1971 | Lissant . |
| 3,640,753 | 2/1972 | Krauch et al. . |
| 3,673,270 | 6/1972 | Gosser . |
| 3,689,585 | 9/1972 | Morikawa . |
| 3,696,108 | 10/1972 | Morikawa . |
| 3,734,867 | 5/1973 | Will . |
| 3,763,056 | 10/1973 | Will . |
| 3,778,390 | 12/1973 | Ulrich . |
| 3,796,767 | 3/1974 | McNulty et al. . |
| 3,806,474 | 4/1974 | Blair . |
| 3,886,225 | 5/1975 | Wilke et al. . |
| 3,897,508 | 7/1975 | Tkatchenko . |
| 3,903,189 | 9/1975 | Hoppstock et al. . |
| 3,917,735 | 11/1975 | Ploner . |
| 3,925,497 | 12/1975 | Josey et al. . |
| 3,954,665 | 5/1976 | Tkatchenko . |
| 3,988,508 | 10/1976 | Lissant . |
| 4,029,100 | 6/1977 | Karami . |
| 4,049,592 | 9/1977 | Marans et al. . |
| 4,093,570 | 6/1978 | Miyake et al. . |
| 4,108,918 | 8/1978 | Hoppstock et al. . |
| 4,108,919 | 8/1978 | Hoppstock et al. . |
| 4,132,839 | 1/1979 | Marans et al. ........................ 521/159 |
| 4,144,153 | 3/1979 | Shikinami et al. .................. 204/159.2 |
| 4,144,278 | 3/1979 | Strope . |
| 4,154,917 | 5/1979 | Miyake et al. ........................ 528/113 |
| 4,180,694 | 12/1979 | Nozaki ..................................... 585/511 |
| 4,219,660 | 8/1980 | Wehrli ...................................... 560/20 |
| 4,229,549 | 10/1980 | Usami et al. ............................ 525/76 |
| 4,229,606 | 10/1980 | Nozaki ..................................... 585/509 |
| 4,234,454 | 11/1980 | Strope ................................ 252/429 R |
| 4,242,531 | 12/1980 | Carter ..................................... 585/512 |
| 4,243,829 | 1/1981 | Pittman, Jr. et al. ................. 585/511 |
| 4,259,468 | 3/1981 | Kajiura et al. ........................ 526/283 |
| 4,262,052 | 4/1981 | Kannan et al. ....................... 428/306 |
| 4,277,633 | 7/1981 | Enomoto et al. ..................... 568/879 |
| 4,283,499 | 8/1981 | Howell ...................................... 521/38 |
| 4,309,387 | 1/1982 | Carter ..................................... 422/201 |
| 4,346,199 | 8/1982 | Peng et al. ............................ 525/316 |
| 4,394,930 | 7/1983 | Korpman .............................. 220/444 |
| 4,412,089 | 10/1983 | Mulder et al. ........................ 585/645 |
| 4,443,568 | 4/1984 | Woo ....................................... 523/406 |
| 4,460,748 | 7/1984 | Rauer ..................................... 525/256 |
| 4,473,611 | 9/1984 | Haq ........................................ 428/198 |
| 4,508,767 | 4/1985 | Hokamura et al. ................ 427/407.1 |
| 4,522,953 | 6/1985 | Barby et al. ............................ 521/64 |
| 4,536,521 | 8/1985 | Haq ........................................ 521/146 |
| 4,536,604 | 8/1985 | Lin et al. ................................ 585/601 |
| 4,588,794 | 5/1986 | Oda et al. ........................... 526/169.2 |
| 4,593,140 | 6/1986 | Mortreux et al. .................... 585/508 |
| 4,603,069 | 7/1986 | Haq et al. ................................ 428/76 |
| 4,606,958 | 8/1986 | Haq et al. ................................ 428/68 |
| 4,611,014 | 9/1986 | Jones et al. ........................... 521/146 |
| 4,612,334 | 9/1986 | Jones et al. ........................... 521/146 |
| 4,617,346 | 10/1986 | Sonoda .................................... 525/68 |
| 4,634,729 | 1/1987 | Pavlin et al. .......................... 524/285 |
| 4,657,973 | 4/1987 | Endo et al. ............................. 525/67 |
| 4,668,709 | 5/1987 | Jones et al. ........................... 521/146 |
| 4,687,876 | 8/1987 | Nozaki .................................... 585/509 |
| 4,694,042 | 9/1987 | McKee et al. ........................... 525/66 |
| 4,709,084 | 11/1987 | Pavlin et al. .......................... 560/118 |
| 4,788,225 | 11/1988 | Edwards et al. ....................... 521/147 |
| 4,791,184 | 12/1988 | Nagai et al. ........................ 526/323.2 |
| 4,797,310 | 1/1989 | Barby et al. ............................. 428/71 |
| 4,818,785 | 4/1989 | Otawa et al. .......................... 524/576 |
| 4,900,706 | 2/1990 | Sasaki et al. .......................... 502/116 |
| 4,943,670 | 7/1990 | Goodall et al. ........................ 585/601 |
| 4,961,982 | 10/1990 | Taylor .................................... 428/41 |
| 4,965,289 | 10/1990 | Sherrington et al. ................ 521/53 |
| 4,966,919 | 10/1990 | Williams, Jr. et al. .............. 526/321 |
| 4,985,467 | 1/1991 | Kelly et al. ............................. 521/52 |
| 4,985,468 | 1/1991 | Elmes et al. ............................ 521/63 |
| 4,990,541 | 2/1991 | Nielsen et al. ......................... 521/70 |
| 5,006,415 | 4/1991 | Matsumaru et al. ................ 428/522 |
| 5,006,592 | 4/1991 | Oshima et al. ....................... 524/504 |
| 5,010,137 | 4/1991 | Umeda et al. ........................ 525/104 |
| 5,021,462 | 6/1991 | Elmes et al. ............................ 521/63 |
| 5,026,807 | 6/1991 | Ohira et al. ........................... 526/321 |
| 5,037,859 | 8/1991 | Williams, Jr et al. ................ 521/55 |

(List continued on next page.)

FOREIGN PATENT DOCUMENTS

| | | |
|---|---|---|
| 0 299 762 A2 | 7/1988 | European Pat. Off. . |
| 0 480 379 A2 | 4/1992 | European Pat. Off. . |
| 2-239863 | 9/1990 | Japan . |
| 2-289608 | 11/1990 | Japan . |
| 3-49759 | 3/1991 | Japan . |
| 1 493 356 | 11/1977 | United Kingdom . |
| 2 078 527 | 1/1982 | United Kingdom . |
| 2 188 055 | 9/1987 | United Kingdom . |
| WO 94/28839 | 12/1994 | WIPO . |

*Primary Examiner*—James J. Seidleck
*Assistant Examiner*—John M. Cooney, Jr.
*Attorney, Agent, or Firm*—Eric W. Guttag; Carl J. Roof; E. Kelly Linman

[57] ABSTRACT

Polymers are made from 1,3,7-octatriene or like conjugated polyenes and a crosslinking agent having at least 2 activated double bonds such as ethylene glycol dimethacrylate. These polymers can be used to make absorbent foams that are useful in absorbent articles such as diapers, as well as latexes that are useful as binders and adhesives.

28 Claims, 6 Drawing Sheets

5,922,780
Page 2

U.S. PATENT DOCUMENTS

| | | | |
|---|---|---|---|
| 5,051,484 | 9/1991 | Sasaki et al. | 526/151 |
| 5,065,752 | 11/1991 | Sessions et al. | 128/156 |
| 5,066,784 | 11/1991 | Sherrington et al. | 530/334 |
| 5,093,426 | 3/1992 | Sakabe et al. | 525/223 |
| 5,110,838 | 5/1992 | Tokiwa et al. | 521/81 |
| 5,116,880 | 5/1992 | Tokiwa et al. | 521/134 |
| 5,135,981 | 8/1992 | Matsumaru et al. | 524/547 |
| 5,147,345 | 9/1992 | Young et al. | 604/378 |
| 5,149,720 | 9/1992 | DesMarais et al. | 521/63 |
| 5,166,224 | 11/1992 | Collins et al. | 522/109 |
| 5,189,070 | 2/1993 | Brownscombe et al. | 521/64 |
| 5,198,472 | 3/1993 | DesMarais et al. | 521/63 |
| 5,200,433 | 4/1993 | Beshouri | 521/64 |
| 5,200,469 | 4/1993 | Hous | 525/245 |
| 5,210,104 | 5/1993 | Bass et al. | 521/64 |
| 5,221,726 | 6/1993 | Dabi et al. | 528/93 |
| 5,250,576 | 10/1993 | DesMarais et al. | 521/63 |
| 5,252,619 | 10/1993 | Brownscombe et al. | 521/64 |
| 5,260,345 | 11/1993 | DesMarais et al. | 521/148 |
| 5,268,224 | 12/1993 | DesMarais et al. | 428/286 |
| 5,290,820 | 3/1994 | Brownscombe et al. | 521/64 |
| 5,318,554 | 6/1994 | Young et al. | 604/378 |
| 5,331,015 | 7/1994 | DesMarais et al. | 521/62 |
| 5,340,842 | 8/1994 | Adamski et al. | 521/150 |
| 5,352,711 | 10/1994 | DesMarais | 521/149 |
| 5,387,207 | 2/1995 | Dyer et al. | 604/369 |
| 5,563,179 | 10/1996 | Stone et al. | 521/64 |

CROSSLINKED POLYMERS MADE FROM 1, 3,7-OCTATRIENE AND LIKE CONJUGATED POLYENES

TECHNICAL FIELD

This application relates to crosslinked polymers made from 1,3,7-octatriene or like conjugated polyenes. This application particularly relates to absorbent foams made from such polymers that are useful in absorbent articles such as diapers.

BACKGROUND OF THE INVENTION

Polymers are used in a wide range of applications due to their stability, elasticity, light weight, strength, ease of fabrication and formulation, and low cost. In applications where flexibility, elasticity, and resilience are desired, amorphous polymers having glass transition temperatures (Tg) below use temperatures (typically about 25° C. or below) are particularly useful. To achieve this, certain types of monomers are selected, often dienes such as isoprene and butadiene. These diene monomers are readily available at low cost and produce low Tg polymers. However, isoprene and 1,3-butadiene have relatively high vapor pressures at ambient temperatures (i.e., 20–25° C.). In addition, 1,3-butadiene is tumorigenic, is explosive when mixed with air, and readily forms the undesired dimer 1-vinyl-4-cyclohexene when heated. These factors make the polymerization of these diene monomers challenging in large scale processes. Accordingly, it would be desirable to use diene monomers that are less volatile and more stable than isoprene or 1,3-butadiene that also produce low Tg polymers.

The flexibility, elasticity and resilience of polymers are useful in many applications, and comprise a variety of forms, including films, fibers, foams and bulk items such as tires. Of particular interest to the present invention are polymeric foams. In addition to containers and packaging, polymeric foams have been used as absorbents in absorbent articles such as diapers and catamenial products. See, for example, U.S. Pat. No. 4,029,100 (Karami), issued Jun. 14, 1977, that discloses a shape-retaining diaper that can employ a foam element in the crotch area of the absorbent pad assembly in order to provide high wet resilience. Certain types of polymeric foams have been used in these absorbent articles for the purpose of imbibing, wicking and/or retaining aqueous body fluids. See, for example, U.S. Pat. No. 3,563,243 (Lindquist), issued Feb. 6, 1971 (absorbent pad for diapers and the like where the primary absorbent is a hydrophilic polyurethane foam sheet); U.S. Pat. No. 4,554,297 (Dabi), issued Nov. 19, 1985 (body fluid absorbing cellular polymers that can be used in diapers or catamenial products); U.S. Pat. No. 4,740,520 (Garvey et al), issued Apr. 26, 1988 (absorbent composite structure such as diapers, feminine care products and the like that contain sponge absorbents made from certain types of super-wicking, crosslinked polyurethane foams).

The use of absorbent foams in absorbent articles such as diapers can be highly desirable. If made appropriately, open-celled hydrophilic polymeric foams can provide features of capillary fluid acquisition, transport and storage required for use in high performance absorbent cores. Absorbent articles containing such foams can possess desirable wet integrity, can provide suitable fit throughout the entire period the article is worn, and can minimize changes in shape during use (e.g., due to swelling, bunching). In addition, absorbent articles containing such foams can be easier to manufacture on a commercial scale. For example, absorbent diaper cores can simply be stamped out of continuous foam sheets and can have considerably greater integrity and uniformity than absorbent fibrous webs. Such foams can also be molded into any desired shape, or even formed into integral, unitary diapers.

Accordingly, it would be desirable to develop polymers that: (1) are flexible, elastic and resilient so as to be useful in making films, adhesives, elastics, and the like; (2) can be made using monomers that are less volatile than isoprene or butadiene; (3) provide low Tg polymers. It would be particularly desirable to be able to make absorbent foams from such polymers that: (a) have adequate or preferably superior absorbency characteristics, including capillary fluid transport capability, so as to be desirable in high performance absorbent cores used in absorbent articles such as diapers, adult incontinence pads or briefs, sanitary napkins and the like; (b) are sufficiently flexible and soft so as to provide a high degree of comfort to the wearer of the absorbent article; and (c) can be manufactured on a commercial scale, at relatively low cost.

DISCLOSURE OF THE INVENTION

The present invention relates to polymers that have relatively low Tgs, are flexible, elastic and resilient, and are made with polyene monomers that are less volatile than isoprene or butadiene. These polymers are made by polymerizing a monomer mixture comprising:

A. from about 30 to about 98% by weight of a polyene having at least 6 carbon atoms and having the formula:

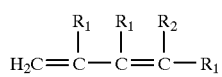

or

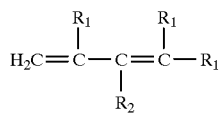

wherein $R_1$ are H, halo, amino, cyano, carboxy, $C_1$–$C_4$ alkyl, $C_1$–$C_4$ alkoxy, $C_1$–$C_4$ ester, $C_6$–$C_{12}$ aryl, $C_4$–$C_{12}$ heteroaryl, or mixtures thereof; $R_2$ is H, halo, amino, hydroxy, cyano, carboxy, $C_1$–$C_{16}$ alkyl, $C_1$–$C_4$ alkoxy, $C_1$–$C_4$ ester, $C_6$–$C_{12}$ aryl, $C_4$–$C_{12}$ heteroaryl, or $C_2$–$C_{12}$ alkenyl;

B. from about 2 to about 70% by weight of a crosslinking agent having at least 2 activated double bonds;

C. up to about 25% by weight other compatible comonomers.

The polymers of the present invention have potentially many uses where flexibility, elasticity and resilience are desired. These polymers are especially useful in the form of open-celled foams for absorbent core structures used in a variety of absorbent articles such as diapers, adult incontinence pads or briefs, sanitary napkins, and the like. These preferred open-celled foams can be prepared by polymerizing a specific type of water-in-oil emulsion having a relatively small amount of an oil phase and a relatively greater amount of a water phase. This type of polymerizable emulsion in general is known in the art as a high internal phase emulsion or "HIPE." The oil phase of these HIPEs comprises the monomer mixture of polyene, crosslinking agent and optional compatible monomer(s), as well as other oil-soluble or miscible adjuvants such as polymerization initiators, antioxidants and plasticizers.

3

DETAILED DESCRIPTION OF THE INVENTION

A. Definitions

Figure 1:
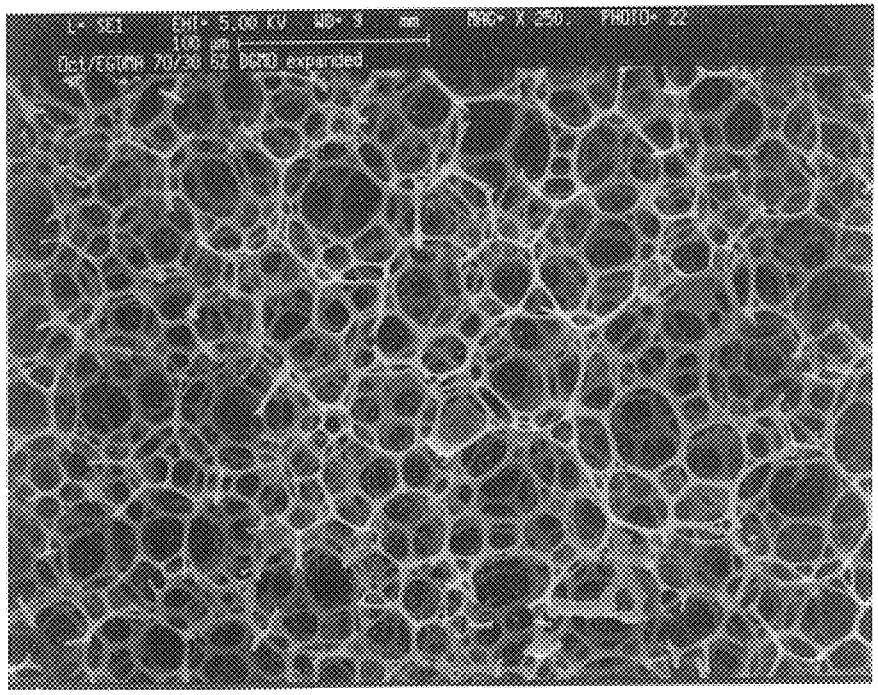
FIG. 1 of the drawings is a photomicrograph (250× magnification) of a section of a polymeric foam made according to the present invention in its expanded state using 1,3,7-octatriene and ethylene glycol dimethacrylate as the monomers.

As used herein, the term "polyene" refers to a compound having two or more carbon-to-carbon double bonds, where two of these double bonds are conjugated in the 1,3-position. The term polyene includes dienes, trienes, tetraenes, etc. The double bonds of the polyene can be cis or trans in the case of dienes, or combinations of cis and trans double bonds in the case of trienes, tetraenes, etc.

As used herein, the term "thermoplastic" refers to polymers that flow and deform under high temperature and pressure without recovery of their original shape. Conversely, as also used herein, the term "thermoset" refers to a polymer that cannot flow under thermal or mechanical stress and is usually crosslinked. See Odian, G. "Principles of Polymerization" 3rd ed., Wiley & Sons: NY, N.Y., 1991, page 109.

As used herein, the terms "elastomer" and "elastomeric" refer to polymers that can undergo very large reversible deformations under applied load. This property appears when either chemical or physical crosslinks are present in the polymeric system. For example, polyisoprene (natural rubber) can be readily formed into a typical elastomer. It is amorphous, easily crosslinked, and has a low Tg. See Odian, G,, "Principles of Polymerization" 3rd ed.; Wiley & Sons: NY, N.Y., 1991, pp 35–37.

As used herein, the term "comprising" means that the various monomers, and other components, or steps, can be

4 conjointly employed in practicing the present invention. Accordingly, the term "comprising" encompasses the more restrictive terms: "consisting essentially of" and "consisting of."

All percentages, ratios and proportions used herein are by weight unless otherwise specified.

B. Monomers

The polymers of the present invention are made from a monomer mixture that comprises: (1) a polyene; (2) a crosslinking agent; and (3) optionally other compatible comonomers.

1. Polyene

The key monomer used in making the polymers of the present invention is a polyene having at least 6 carbon atoms (preferably from 6 to 20 carbon atoms, most preferably from 6 to 10 carbon atoms) and having the formula:

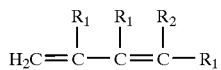

or

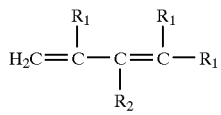

wherein $R_1$ are H, halo, carboxy, $C_1C_4$ alkyl, $C_1$–$C_4$ alkoxy, $C_1$–$C_4$ ester, $C_6$–$C_{12}$ aryl, $C_4$–$C_{12}$ heteroaryl, or mixtures thereof; $R_2$ is H, halo, carboxy, $C_1$–$C_{16}$ alkyl, $C_1$–$C_4$ alkoxy, $C_1$–$C_4$ ester, $C_6$–$C_{12}$ aryl, $C_4$–$C_{12}$ heteroaryl, or $C_2$–$C_{12}$ alkenyl. The various $R_1$ and $R_2$ substituents can be substituted (e.g., hydroxyalkyl), can be unsubstituted, or can be mixtures of substituted and unsubstituted. Suitable polyenes according to the above formula include 1,3-hexadiene, 1,3-heptadiene, 1,3-octadiene, 1,3-nonadiene, 1,3-decadiene, 1,3-undecadiene, 1,3-dodecadiene, 2-methyl-1,3-hexadiene, 6-methyl-1,3-heptadiene, 7-methyl-1,3-octadiene, 1,3,7-octatriene, 1,3,9-decatriene, 1,3,6-octatriene, 2,3-dimethyl-1,3-butadiene, 2-amyl-1,3-butadiene, 2,6-dimethyl-1,3,7-octatriene, 2,7-dimethyl-1,3,7-octatriene, 2,6-dimethyl-1,3,6-octatriene, 2,7-dimethyl-1,3,6-octatriene, 7-methyl-3-methylene-1,6-octadiene (myrcene), 2,6dimethyl-1,5,7-octatriene (ocimene), 1-methyl-2-vinyl-4,6-hepta-dieny-3,8-nonadienoate, 5-methyl-1,3,6-heptatriene, 2-ethyl-1,3-butadiene, and mixtures thereof.

Preferred polyenes for making polymers according to the present invention have from about 6 to about 10 carbon atoms and have the formula:

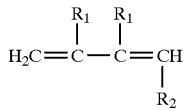

or

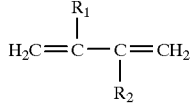

wherein $R_1$ is H, $C_1$–$C_4$ alkyl, $C_1$–$C_4$ alkenyl, or $C_1$–$C_4$ alkoxy; $R_2$ is H, $C_1$–$C_4$ alkyl, $C_1$–$C_4$ alkenyl or $C_1$–$C_4$ alkoxy. Examples of preferred polyenes include 1,3- hexadiene, 1,3-octadiene, 2,3-dimethyl-1,3-butadiene, 2-ethyl-1,3-butadiene, 2-amyl-1,3-butadiene, myrcene, and particularly 1,3,7-octatriene.

2. Crosslinking Agent

Another monomer used in making the polymers of the present invention is a crosslinking agent having at least 2 activated double bonds. By "activated double bonds" is meant that the crosslinking agent has a moiety adjacent to the double bond capable of stabilizing the incipient radical or charge on the carbons of the double bond. Suitable crosslinking agents useful in polymers of the present invention include any of those that can be employed in crosslinking diene monomers, such as divinylbenzenes, divinyltoluenes, divinylxylenes, divinylnaphthalenes divinylalkylbenzenes, divinylphenanthrenes, trivinylbenzenes, divinylbiphenyls, divinyidiphenylmethanes, divinylbenzyls, divinylphenylethers, divinyldiphenylsulfides, divinylfurans, divinylsulfone, divinylsulfide, divinyidimethylsilane, 1,1'-divinylferrocene, 2-vinylbutadiene, di-, tri-, tetra-, penta- and higher acrylates, acrylamides, methacrylates, and methacrylamides, N-methylolacrylamide, N-methylolmethacrylamide, and the like, as well as mixtures of these crosslinking agents. Higher levels of most of these crosslinking agents tend to increase the Tg of the resultant polymer as well as its strength with resultant loss of flexibility and resilience. This emphasizes the need for the polyene described above to be able to form a homopolymer having a sufficiently low Tg so that the crosslinked polymer of the present invention is still adequately flexible and resilient for the desired use.

A particularly suitable class of crosslinking agents according to the present invention have following formula:

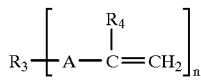

wherein A is a linking group that activates the double bond; $R_3$ is $C_1$–$C_{12}$ alkylene, $C_2$–$C_{12}$ alkenylene, $C_6$–$C_{12}$ arylene, $C_7$–$C_{18}$ arylalkylene, $C_4$–$C_{12}$ heteroarylene, $C_6$–$C_{18}$ heteroarylalkylene, $C_8$–$C_{18}$ arylalkenylene, or $C_8$–$C_{18}$ heteroarylalkenylene; $R_4$ is H, halo, carboxy, $C_1$–$C_4$ alkyl, $C_1$–$C_4$ alkoxy, $C_{1-C4}$ ester, $C_6$–$C_{12}$ aryl or $C_4$–$C_{12}$ heteroaryl; n is at least 2. The $R_3$ and various $R_4$ substituents can be substituted (e.g., hydroxyalkyl), can be unsubstituted, or can be mixtures of substituted and unsubstituted. Linking groups A are typically carboxy ester groups, amide groups, carbonate ester groups, sulfonate ester groups, phosphonate ester groups, carboxy anhydride groups, sulfonic anhydride groups, ether groups, thioether groups, carbon-to-carbon double bond (e.g., olefinic) groups, and the like.

Particularly suitable linking groups A include carboxy ester groups, amide groups, and ether groups. Particularly preferred crosslinking agents having carboxy ester or amide linking groups include di-, tri-, and tetra-(meth)acrylates, and di-, tri-, and tetra-(meth)acrylamides. Representative examples of such crosslinking agents include ethylene glycol dimethacrylate, neopentyl glycol dimethacrylate, 1,3-butanediol dimethacrylate, 1,4-butanediol dimethacrylate, diethylene glycol dimethacrylate, hydroquinone dimethacrylate, catechol dimethacrylate, resorcinol dimethacrylate, triethylene glycol dimethacrylate, polyethylene glycol dimethacrylate; trimethylolpropane trimethacrylate, pentaerythritol tetramethacrylate, 1,3-butanediol diacrylate, 1,4-butanediol diacrylate, 1,6-hexanediol diacrylate, tetramethylene diacrylate, trimethy-olpropane triacrylate, pentaerythritol tetraacrylate, N-methylolacrylamide, 1,2-ethylene bisacrylamide, 1,4-butane bisacrylamide, and mixtures thereof.

Most preferred crosslinking agents according to the present invention having carboxy ester linking groups are acrylates or methacrylates having the formula:

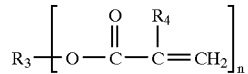

wherein $R_3$ is $C_2$–$C_6$ alkylene or oxyalkylene; $R_4$ is H or methyl; and n is 2 to 4. Particularly preferred crosslinking agents according to the above formula include ethylene glycol diacrylate and dimethacrylate, diethylene glycol diacrylate and dimethacrylate, 1,6-hexanediol diacrylate and dimethacrylate, 2-butenediol diacrylate and dimethacrylate, ethylene glycol trimethylolpropane triacrylate and trimethacrylate, and mixtures thereof.

3. Other Compatible Comonomers

Polymers according to the present invention can be made using other compatible comonomers in addition to the polyene and optional crosslinking agents. These optional compatible comonomers typically modify the glass transition (Tg) properties of the resulting polymer, its modulus (strength), and its toughness. Suitable optional comonomers include those having a double bond that will copolymerize with the polyene, and/or crosslinking agent. Illustrative copolymerizable monomers of this type include chloroprene, tetrafluoroethylene, chlorotrifluoroethylene, hexafluoropropylene, styrene, o-methoxystyrene, p-methoxystyrene, m-methoxystyrene, o-methyl styrene, o-phenyl styrene, vinyl naphthalene, vinyl chloride, vinyl fluoride, vinylidene chloride, vinylidene fluoride, vinylidene bromide, acrylic and alpha-alkyl acrylic acids, and the esters, amides and nitriles thereof, such as acrylic acid, chloroacrylic acid, methacrylic acid, methyl acrylate, ethyl acrylate, butyl acrylate, n-octyl acrylate, 2-ethylhexyl acrylate, methyl methacrylate, butyl methacrylate, octyl methacrylate, nonyl methacrylate, decyl methacrylate, isodecyl methacrylate, dodecyl (lauryl) methacrylate, tetradecyl methacrylate, acrylamide, N-methylacrylamide, N,N-dimethylacrylamide, N,N-dimethyl-methacrylamide, acrylonitrile, methacrylonitrile, and the like; maleic and fumaric acids, their anhydrides, and their alkyl esters such as maleic anhydride, dimethyl maleate, and the like; vinyl alkyl ethers and ketones such as vinyl methyl ether, vinyl ethyl ether, vinyl isobutyl ether, methyl vinyl ketone, ethyl vinyl ketone, and isobutyl vinyl ketone; dienes such as butadiene, isoprene, piperylene, cyclopentadiene, norbornadiene, and dicyclopentadiene; vinylpyridine; N-vinylcarbazole; N-vinylpyrrolidine; acrolein; vinylferrocene, vinyltitanocene, methyl vinylsulfone, vinylpyridine, 2-vinylbutadiene, and the like, as well as mixtures of these monomers.

C. Preparation of Polymers

1. In General

Polymers according to the present invention are generally prepared from a monomer, or combination of monomers, with a suitable initiator. Polymerization can take place in one phase or two, with the initiator in either phase. Suitable initiators include anionic initiators (e.g., alkyl lithium), cationic initiators (e.g., metal chlorides), coordination catalysts, or free radical initiators. Anionic initiators in inert solvents are useful for preparing block copolymers such as those used as elastomers and adhesives. Free radical initiators are useful in solution and bulk polymerizations, as well as two phase systems comprising monomers dispersed in water (latex, emulsion, or suspension type). Typically, heat and/or certain transition metals are used to activate this free radical system. For a general description of processes for preparing polymers according to the present invention, see Odian, supra and McGrath, J. E.; *J. Chem. Ed.*, 1981, 58(11), 844–861.

Besides the monomers and the initiator, various optional adjuvants can be used in preparing polymers according to the present invention. These optional adjuvants typically are included for the purpose of modifying the stability, color, strength, or other properties of the resultant polymer. Suitable adjuvants include antioxidants such as Hindered Amine Light Stabilizers (HALS) such as bis-(1,2,2,5,5-pentamethylpiperidinyl) sebacate (Tinuvin 765), and Hindered Phenolic Stabilizers (HBPS) such as Irganox 1076 and t-butylhydroxyquinone. Other adjuvants include, dyes, pigments, flame retardants fillers such as carbon black, calcium carbonate, silicates, and other particulate additives well known to those skilled in the art, preformed polymers such as polyisoprene, and plasticizers. Suitable plasticizers include dioctyl azelate, dioctyl sebacate, or dioctyl adipate and other long chain length alkyl esters of di-, tri-, and tetra-carboxylic acids such as azelaic, sebacic, adipic, phthalic, terephthalic, isophthalic, and the like. Effective amounts of these plasticizers are typically in the range of from about 5 to 30% by weight of the polymer, more typically from about 7 to about 15% by weight of the polymer. In a preferred process for producing a crosslinked polymer according to the present invention, a mixture of polymerizable monomers comprising from about 50 to about 95% by weight of a polyene, from about 5 to about 50% by weight of a crosslinking agent and up to about 25% by weight of other compatible comonomer (as previously described) is polymerized in the presence of an antioxidant (as previously described) and a polymerization initiator (as previously described).

Because the monomer mixture includes a crosslinking agent, the polymers prepared according to the present invention are thermosetting. These thermosetting polymers will not flow at higher temperatures to any large degree, are generally not extrudable and are generally amorphous. Thermosets have the advantage of being relatively immune to stress relaxation or creep at temperatures above the Tg of the polymer. To the extent that creep or stress relaxation occur in these thermosets, the effect is not permanent and upon release of the deforming load, the thermoset will return to its original shape and strength. Thermosets also have the property of being insoluble in any solvent unless chemical degradation occurs. When exposed to some solvents, thermosets can swell considerably and imbibe the solvent. However, no true solution can occur as long as the crosslinks remain intact.

2. Emulsion Polymerization.

Emulsified polymers or latexes according to the present invention can be prepared by polymerization of certain oil-in-water emulsions having about equal volumes of water and oil. Emulsions of this general type are well known in the art. See *Encyclopedia of Polymer Science and Engineering*, Volume 8, (Second Edition, Wiley & Sons, New York, N.Y., 1988), page 647. The chemical nature and properties of the latex are determined by the type of polyenes, crosslinking agents, and comonomers present in the emulsion:

a. Oil Phase Components

The monomer component present in the oil phase of the emulsion normally comprises: (1) from about 50 to about 98%, more preferably from about 60 to about 75%, most preferably from about 65 to about 70%, of one or more polyenes as previously described; (2) from about 2 to about 50%, more preferably from about 5 to about 20%, most preferably from about 6 to about 10%, of one or more of the crosslinking agents as previously described; and (3) optionally a comonomer as previously described in amounts ranging up to about 25%.

The oil phase can optionally comprise an oil soluble free radical initiator, such as azoisobutyronitrile (AIBN). The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase. Other optional adjuvants include antioxidants, fillers, dyes, pigments, plasticizers, processing aids, and the like well known to those skilled in the art. See *Encyclopedia of Polymer Science and Engineering*, ibid., pp. 665–666.

b. Water Phase Components

The continuous water phase of the emulsion generally comprises one or more dissolved components. One important component is a surfactant, usually a hydrophilic surfactant having a high HLB value, i.e., from about 10 to about 20, preferably from about 15 to about 20. One such preferred surfactant is a sulfonated linear alkyl benzene sulfonate (LAS). However, many other similar surfactants well known to those skilled in the art can be used as well. Other optional components include water soluble free radical initiators such as potassium persulfate (if no oil soluble initiator is used), and electrolytes. The electrolyte can be any inorganic salt capable of imparting ionic strength to the aqueous phase. Preferred electrolytes are those discussed hereafter in the section on HIPE-type emulsions.

c. Formation of the Latex

Emulsion polymerization typically involves the steps of: 1) forming an oil-in-water emulsion; and 2) polymerizing or curing the emulsion. The emulsion is typically formed by combining the water and oil phases under high shear to make a thin, generally white emulsion roughly the consistency and appearance of milk. The polymerization or curing step typically involves storage at elevated temperatures for a period of time sufficient to complete the free radical polymerization process. This yields a generally phase stable milky emulsion of cured colloidal polymer particles in a continuous water phase.

3. Bulk Polymers.

Bulk polymers according to the present invention can be prepared by simply combining the monomers with a suitable initiator, often followed by heating to expedite the polymerization reaction. A representative example would be the combination of 1,3,7-octatriene and ethylene glycol dimethacrylate (70:30 weight ratio) with azoisobutyronitrile (AIBN) as the initiator, followed by heating overnight at 60° C. The resulting product is a clear flexible polymer. Antioxidants such as Tinuvin 765 or Irganox 1076 can be added prior to polymerization. The flexibility of the product can be modified by addition of plasticizer(s) prior to the polymerization, as described above. The product can also be allowed conform to the shape of the reaction vessel if a specific shape is desired.

4. Solution Polymers.

Solution polymers according to the present invention can be prepared much like bulk polymers except that the precursor monomers and initiator(s) are dissolved in an unreactive solvent phase such as tetrahydrofuran or benzene (to be chemically compatible with the initiating species). Removal of solvent yields the final polymeric product.

5. Suspension Polymers

Suspension polymers according to the present invention can be prepared much like emulsion polymers, except that polyvinyl alcohol or other suspending agents are used to suspend the forming polymer. The reaction mixture is also agitated throughout the reaction.

6. HIPE Foams

Polymeric foams according to the present invention can be prepared by polymerization of certain water-in-oil emulsions having a relatively high ratio of water phase to oil phase. Emulsions of this type that have these relatively high water to oil phase ratios are commonly known in the art as high internal phase emulsions ("HIPEs"or "HIPE" emulsions). The polymeric foam materials which result from the polymerization of such emulsions are referred to hereafter as "HIPE foams."

The relative amounts of the water and oil phases used to form the HIPEs are important in determining the structural, mechanical and performance properties of the resulting polymeric foams. In particular, the ratio of water to oil in the emulsion can influence the density, cell size, and capillary absorption pressure of the foam, as well as the dimensions of the struts that form the foam. The emulsions used to prepare these HIPE foams will generally have water-to-oil phase ratios ranging from about 12:1 to about 100:1, more preferably from about 20:1 to about 70:1, most preferably from about 25:1 to about 50:1.

a. Oil Phase Components

The monomer component present in the oil phase of the HIPE comprises one or more polyenes as previously described. The polyene(s) will normally comprise from about 30 to about 95%, more preferably from about 60 to about 90%, most preferably from about 65 to about 80%, of the monomer component.

The monomer component also optionally comprises one or more crosslinking agents. The crosslinking agent will generally comprise from 5 to about 70%, more preferably from about 10 to about 40%, most preferably from about 20 to about 35%, of the monomer component.

Depending upon the type and amounts of polyene(s), monomers and crosslinking agents used, and depending further upon the desired characteristics of the resulting polymeric foams, the comonomers can be selected from any of those previously described. The comonomer of whatever type will generally be employed in the oil phase of the HIPE in an amount up to about 25%, more preferably up to about 20%, of the monomer component Another essential component of the oil phase is an emulsifier that permits the formation of stable HIPEs. Such emulsifiers include those which are soluble in the oil phase of the emulsion. These emulsifiers can also plasticize and/or hydrophilize the resulting polymeric foam. These emulsifiers are typically nonionic and include the diglycerol monoesters of branched $C_{16}$–$C_{24}$ fatty acids, linear unsaturated $C_{16}$–$C_{22}$ fatty acids, or linear saturated $C_{12}$–$C_{14}$ fatty acids, such as diglycerol monooleate (i.e., diglycerol monoesters of $C_{18:1}$ fatty acids), diglycerol monomyristate, diglycerol monoisostearate, and diglycerol monoesters of coconut fatty acids; sorbitan monoesters of branched $C_{16}$–$C_{24}$ fatty acids, linear unsaturated $C_{16}$–$C_{22}$ fatty acids, and linear saturated $C_{12}$–$C_{14}$ fatty acids, such as sorbitan monooleate, sorbitan monomyristate, and sorbitan monoesters derived from coconut fatty acids; diglycerol monoaliphatic ethers of branched $C_{16}$–$C_{24}$ alcohols (e.g. Guerbet alcohols), linear unsaturated $C_{16}$–$C_{22}$ alcohols, and linear saturated $C_{12}$–$C_{14}$ alcohols (e.g., coconut fatty alcohols), and mixtures of these emulsifiers. Preferred emulsifiers include diglycerol monooleate, diglycerol monoisostearate, diglycerol monomyristate, the cocoyl (e.g., lauryl and myristoyl) ethers of diglycerol, sorbitan laurate (e.g., SPAN® 20), sorbitan monooleate (e.g., SPAN® 80), and mixtures thereof.

For the certain preferred emulsifier systems comprising a diglycerol monooleate, coemulsifiers such as diglycerol monoisostearate can be employed, usually at a weight ratio of diglycerol monooleate:diglycerol monoisostearate within the range of from about 10:1 to about 1:10. Preferably, this weight ratio is in the range of from about 4:1 to about 1:1.

Diglycerol monoesters of linear unsaturated and branched fatty acids useful as emulsifiers in the present invention can be prepared by esterifying diglycerol with fatty acids, using procedures well known in the art. See, for example, the method for preparing polyglycerol esters disclosed in copending U.S. application Ser. No. 07/989,270 (Dyer et al), filed Dec. 11, 1992, which is incorporated by reference. Diglycerol can be obtained commercially or can be separated from polyglycerols that are high in diglycerol. Linear unsaturated and branched fatty acids can be obtained commercially. The mixed ester product of the esterification reaction can be fractionally distilled under vacuum one or more times to yield distillation fractions that are high in diglycerol monoesters. For example, a A CMS-15A (C.V.C. Products Inc.; Rochester, N.Y.) continuous 14 inch centrifugal molecular still can be used for fractional distillation. Typically, the polyglycerol ester feedstock, while being heated, is first metered through a degasser unit and then to the heated evaporator cone of the still, where the vacuum distillation takes place. Distillate is collected on the bell jar surface, which can be heated to facilitate distillate removal. Distillate and residue are continuously removed by transfer pumps. The fatty acid composition of the resultant mixed ester product can be determined using high resolution gas chromatography. See copending U.S. application Ser. No. 07/989,270 (Dyer et al), filed Dec. 11, 1992, which is incorporated by reference. Polyglycerol and polyglycerol ester distribution of the resultant mixed ester product can be determined by capillary supercritical chromatography. See copending U.S. application Ser. No. 07/989,270 (Dyer et al), filed Dec. 11, 1992, which is incorporated by reference.

Linear saturated, linear unsaturated, or branched diglycerol monoaliphatic ethers can also be prepared and their composition determined using procedures well known in the art. See also copending U.S. application Ser. No. 08/370,920 (Stephen A. Goldman et al), filed Jan. 10, 1995, which is incorporated by reference.

Sorbitan monoesters of linear unsaturated and branched fatty acids can be obtained commercially or prepared using methods known in the art. See, for example, U.S. Pat. No. 4,103,047 (Zaki et al), issued Jul. 25, 1978 (herein incorporated by reference), especially column 4, line 32 to column 5, line 13. The mixed sorbitan ester product can be fractionally vacuum distilled to yield compositions that are high in sorbitan monoesters. Sorbitan ester compositions can be determined by methods well known in the art such as small molecule gel permeation chromatography. See copending U.S. application Ser. No. 08/370,920 (Stephen A. Goldman et al), filed Jan. 10, 1995, (herein incorporated by reference), which describes the use of this method for polyglycerol monoaliphatic ethers.

The oil phase used to form the HIPEs will generally comprise from about 65 to about 98% by weight monomer component and from about 2 to about 35% by weight emulsifier component. Preferably, the oil phase will comprise from about 80 to about 97% by weight monomer component and from about 3 to about 20% by weight emulsifier component.

In addition to the monomer and emulsifier components, the oil phase can contain other optional components. One such optional component is an oil soluble polymerization initiator of the general type well known to those skilled in the art, such as described in U.S. Pat. No. 5,290,820 (Bass et al), issued Mar. 1, 1994, which is incorporated by reference. A preferred optional component is an antioxidant such as a Hindered Amine Light Stabilizer (HALS) and Hindered Phenolic Stabilizers (HPS) as previously described or any other antioxidant compatible with the initiator system to be employed. Another preferred optional component is a plasticizer such as dioctyl azelate, dioctyl sebacate or dioctyl adipate, as previously described. Other optional components include fillers, colorants, fluorescent agents, opacifying agents, chain transfer agents, and the like, as described above.

b. Water Phase Components

The dispersed internal water phase of the HIPE is generally an aqueous solution containing one or more dissolved components. One essential dissolved component of the water phase is a water-soluble electrolyte. The dissolved electrolyte minimizes the tendency of polyenes, crosslinkers, and comonomers that are primarily oil soluble to also dissolve in the water phase. This, in turn, is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred polymeric foams can be open-celled.

Any electrolyte capable of imparting ionic strength to the water phase can be used. Preferred electrolytes are mono-, di-, or trivalent inorganic salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in the present invention. Generally the electrolyte will be utilized in the water phase of the HIPEs in a concentration in the range of from about 0.2 to about 20% by weight of the water phase. More preferably, the electrolyte will comprise from about 1 to about 10% by weight of the water phase.

The HIPEs will also typically contain a polymerization initiator. Such an initiator component is generally added to the water phase of the HIPE and can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts.

The initiator material can be present at up to about 20 mole percent based on the total moles of polymerizable monomers present in the oil phase. More preferably, the initiator is present in an amount of from about 0.001 to 10 mole percent based on the total moles of polymerizable monomers in the oil phase.

c. Hydrophilizing Surfactants and Hydratable Salts

The polymer forming the HIPE foam structure will preferably be substantially free of polar functional groups. This means the polymeric foam will be relatively hydrophobic in character. These hydrophobic foams can find utility where the absorption of hydrophobic fluids is desired. Uses of this sort include those where an oily component is mixed with water and it is desired to separate and isolate the oily component, such as in the case of oil spills.

When these foams are to be used as absorbents for aqueous fluids such as juice spills, milk, and the like and/or body fluids such as urine and/or menses, they generally require further treatment to render the foam relatively more hydrophilic. This can generally be accomplished by treating the HIPE foam with a hydrophilizing surfactant in a manner described more fully hereafter.

These hydrophilizing surfactants can be any material that enhances the water wettability of the polymeric foam. They are well known in the art, and can include a variety of surfactants, preferably of the nonionic type. They will generally be liquid form, and can be dissolved or dispersed in a hydrophilizing solution that is applied to the HIPE foam surface. In this manner, hydrophilizing surfactants can be adsorbed by the preferred HIPE foams in amounts suitable for rendering the surfaces thereof substantially hydrophilic, but without substantially impairing the desired flexibility and compression deflection characteristics of the foam. Such surfactants can include all of those previously described for use as the oil phase emulsifier for the HIPE, such as diglycerol monooleate and diglycerol monoisostearate. Such hydrophilizing surfactants can be incorporated into the foam during HIPE formation and polymerization, or can be incorporated by treatment of the polymeric foam with a solution or suspension of the surfactant in a suitable carrier or solvent. In preferred foams, the hydrophilizing surfactant is incorporated such that residual amounts of the surfactant that remain in the foam structure are in the range from about 0.5 to about 10%, preferably from about 0.5 to about 6%, by weight of the foam.

Another material that typically needs to be incorporated with these surfactants into the HIPE foam structure is a hydratable, and preferably hygroscopic or deliquescent, water soluble inorganic salt, especially if the foam is to remain in a relatively thin (collapsed) state after drying. Such salts include, for example, toxicologically acceptable alkaline earth metal salts. Salts of this type and their use with oil-soluble surfactants as the foam hydrophilizing agent is described in greater detail in U.S. Pat. No. 5,352,711 (DesMarais), issued Oct. 4, 1994, the disclosure of which is incorporated by reference. Preferred salts of this type include the calcium halides such as calcium chloride that, as previously noted, can also be employed as the water phase electrolyte in the HIPE.

Hydratable inorganic salts can easily be incorporated by treating the foams with aqueous solutions of such salts. These salt solutions can generally be used to treat the foams after completion of, or as part of, the process of removing the residual water phase from the just-polymerized foams. Treatment of foams with such solutions preferably deposits hydratable inorganic salts such as calcium chloride in residual amounts of at least about 0.1% by weight of the foam, and typically in the range of from about 0.1 to about 12%, preferably from about 7 to about 10%, by weight of the foam.

Treatment of these relatively hydrophobic foams with hydrophilizing surfactants (with or without hydratable salts) will typically be carried out to the extent necessary to impart suitable hydrophilicity to the foam. Some foams of the preferred HIPE type, however, are suitably hydrophilic as prepared, and can have incorporated therein sufficient amounts of hydratable salts, thus requiring no additional treatment with hydrophilizing surfactants or hydratable salts. In particular, such preferred HIPE foams include those where certain oil phase emulsifiers previously described and calcium chloride are used in the HIPE. In those instances, the foam will be suitably hydrophilic, and will include residual water-phase liquid containing or depositing sufficient amounts of calcium chloride, even after the foam has been dewatered to a practicable extent.

d. Processing Conditions for Obtaining HIPE Foams

Foam preparation typically involves the steps of: 1) forming a stable high internal phase emulsion (HIPE); 2) polymerizing/curing this stable emulsion under conditions suitable for forming a solid polymeric foam structure; 3) optionally washing the solid polymeric foam structure to remove the original residual water phase from the polymeric foam structure and, if necessary, treating the polymeric foam structure with a hydrophilizing agent and/or hydratable salt to deposit any needed hydrophilizing agent/hydratable salt, and 4) thereafter dewatering this polymeric foam structure.

(1). Formation of HIPE

The HIPE is formed by combining the oil and water phase components in the previously specified weight ratios. The oil phase will typically contain the requisite polyenes, crosslinkers, comonomers and emulsifiers, as well as optional components such as plasticizers, antioxidants, flame retardants, and chain transfer agents. The water phase will typically contain electrolytes and polymerization initiators, as well as optional components such as water-soluble emulsifiers.

The HIPE can be formed by subjecting the combined oil and water phases to shear agitation. Shear agitation is generally applied to the extent and for a time period necessary to form a stable emulsion. Such a process can be conducted in either batchwise or continuous fashion and is generally carried out under conditions suitable for forming an emulsion where the water phase droplets are dispersed to such an extent that the resulting polymeric foam will have the requisite cell size and other structural characteristics. Emulsification of the oil and water phase combination will frequently involve the use of a mixing or agitation device such as a pin impeller.

One preferred method of forming such HIPEs involves a continuous process that combines and emulsifies the requisite oil and water phases. In such a process, a liquid stream comprising the oil phase is formed. Concurrently, a separate liquid stream comprising the water phase is also formed. The two separate streams are then combined in a suitable mixing chamber or zone such that the desired water to oil phase weight ratios are achieved.

In the mixing chamber or zone, the combined streams are generally subjected to shear agitation provided, for example, by a pin impeller of suitable configuration and dimensions. Once formed, the stable liquid HIPE can be withdrawn from the mixing chamber or zone. This preferred method for forming HIPEs via a continuous process is described in greater detail in U.S. Pat. No. 5,149,720 (DesMarais et al), issued Sep. 22, 1992, which is incorporated by reference. See also copending U.S. application Ser. No. 08/370,694 Thomas A. DesMarais), filed Jan. 10, 1995 (herein incorporated by reference), which describes an improved continuous process having a recirculation loop for the HIPE which is incorporated by reference.

(2). Polymerization/Curing of the HIPE

The HIPE formed will generally be collected in a suitable reaction vessel. In one embodiment, the reaction vessel comprises a tub constructed of polyethylene from which the eventually polymerized/cured solid foam material can be easily removed for further processing after polymerization/curing has been carried out to the extent desired. The temperature at which the HIPE is poured into the vessel is preferably approximately the same as the polymerization/curing temperature.

Suitable polymerization/curing conditions will vary depending upon the monomer and other makeup of the oil and water phases of the emulsion (especially the emulsifier systems used), and the type and amounts of polymerization initiators used. Frequently, however, suitable polymerization/curing conditions will involve maintaining the HIPE at temperatures above about 30° C., more preferably above about 35° C., for a time period ranging from about 2 to about 64 hours, more preferably from about 4 to about 48 hours. The HIPE can also be cured in stages such as described in U.S. Pat. No. 5,189,070 (Brownscombe et al), issued Feb. 23, 1993, which is herein incorporated by reference.

A porous water-filled open-celled HIPE foam is typically obtained after polymerization/curing in a reaction vessel, such as a tub. This polymerized HIPE foam is typically cut or sliced into a sheet-like form. Sheets of polymerized HIPE foam are easier to process during subsequent treating/washing and dewatering steps, as well as to prepare the HIPE foam for use in absorbent articles. The polymerized HIPE foam is typically cut/sliced to provide a cut thickness in the range of from about 0.08 to about 2.5 cm. During subsequent dewatering, this can lead to collapsed HIPE foams having a thickness of from about 10 to about 17% of this cut thickness.

(3). Treating/Washing HIPE Foam

The polymerized HIPE foam formed will generally be filled with residual water phase material used to prepare the HIPE. This residual water phase material (generally an aqueous solution of electrolyte, residual emulsifier, and polymerization initiator) should be at least partially removed prior to further processing and use of the foam. Removal of this original water phase material can be conveniently carried out by compressing the foam structure to squeeze out residual liquid and/or by washing the foam structure with water or other aqueous washing solutions. Frequently several compressing and washing steps, e.g., from 2 to 4 cycles, can be used.

The dewatered HIPE foam can be treated by continued washing, with an aqueous solution of a suitable hydrophilizing surfactant and/or hydratable salt. Hydrophilizing surfactants and hydratable salts that can be employed have been previously described and include sorbitan laurate (e.g., SPAN® 20) and calcium chloride. See U.S. Pat. No. 5,292,777 (DesMarais et al), issued Mar. 8, 1994, which is incorporated by reference.

(4). Foam Dewatering

Dewatering can be achieved by compressing the foam to squeeze out residual water, by subjecting the foam, or the water therein to temperatures of from about 60° C. to about 200° C., or to microwave treatment, by vacuum dewatering or by a combination of compression and thermal drying/microwave/vacuum dewatering techniques. The dewatering step will generally be carried out until the HIPE foam is ready for use and is as dry as practicable. Frequently such compression dewatered foams will have a water (moisture) content of from about 50 to about 500%, more preferably from about 50 to about 200%, by weight on a dry weight basis. Subsequently, the compressed foams can be thermally dried to a moisture content of from about 5 to about 40%, more preferably from about 5 to about 15%, on a dry weight basis.

e. Characteristics of HIPE foams.

Polymeric foams according to the present invention useful in absorbent articles and structures are those which are relatively open-celled. This means the individual cells of the foam are in complete, unobstructed communication with adjoining cells. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 1–2 and 5–6. For purposes of the present invention, a foam material is "open-celled" if at least 80% of the cells in the foam structure that are at least 1 μm size are in fluid communication with at least one adjacent cell.

In addition to being open-celled, these polymeric foams can be sufficiently hydrophilic to permit the foam to absorb aqueous fluids. The foam structures are rendered hydrophilic by residual hydrophilizing agents left therein after polymerization, or by selected post-polymerization foam treatment procedures, as previously described. The extent to which these polymeric foams are "hydrophilic" can be quantified by the "adhesion tension" value exhibited when in contact with an absorbable test liquid. Such a procedure is described in the TEST METHODS section of copending U.S. application Ser. No. 07/989,270 (Dyer et al), filed Dec. 11, 1992, which is incorporated by reference. Foams which are useful as absorbents in the present invention are generally those which exhibit an adhesion tension value of from about 15 to about 65 dynes/cm, more preferably from about 20 to about 65 dynes/cm, as determined by capillary absorption of synthetic urine having a surface tension of 65±5 dynes/cm.

The polymeric foams of the present invention can be prepared in the form of collapsed (i.e. unexpanded), polymeric foams that, upon contact with aqueous fluids, expand and absorb such fluids. As previously described, these collapsed polymeric foams are usually obtained by expressing water from the resultant polymerized HIPE through compressive forces, and/or thermal drying or vacuum dewatering. After compression, and/or thermal drying/vacuum dewatering, the polymeric foam is in a collapsed, or unexpanded state.

Figure 2:
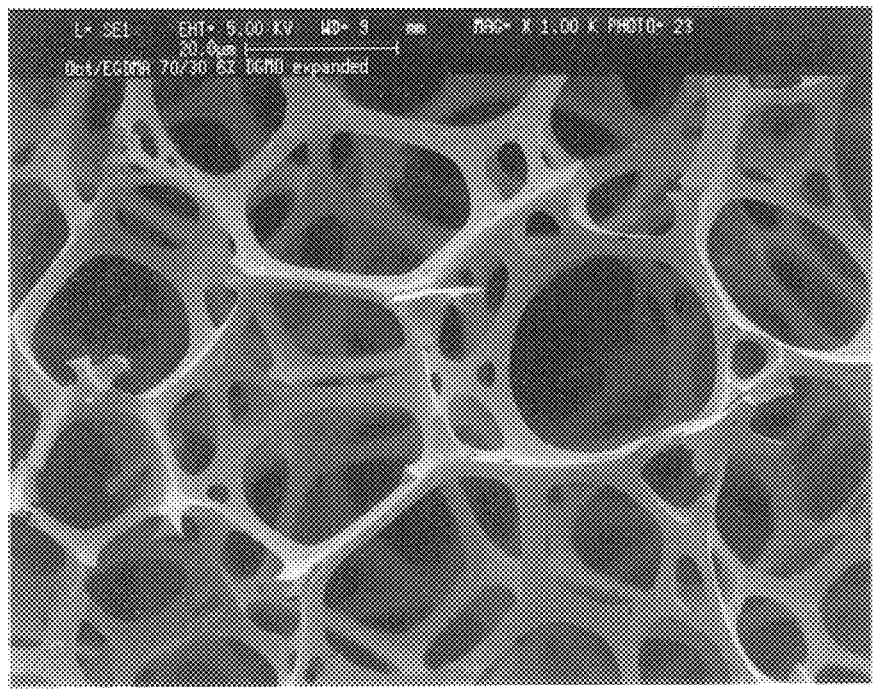
FIG. 2 of the drawings is a photomicrograph (1000× magnification) of the polymeric foam shown in FIG. 1.
Figure 3:
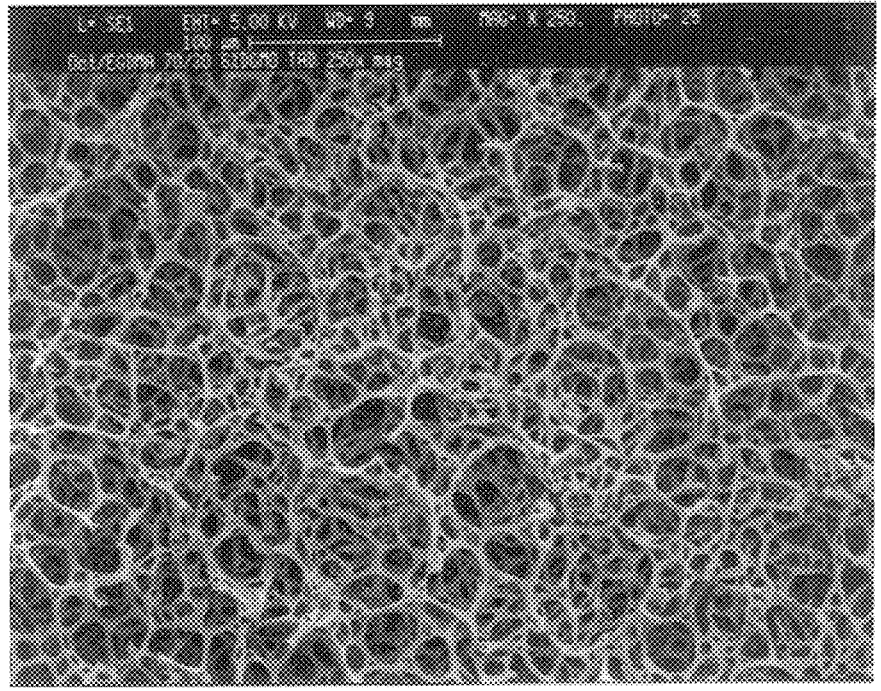
FIG. 3 of the drawings is a photomicrograph (250× magnification) of a section of a polymeric foam made according to the present invention in its collapsed state using 1,3,7-octatriene and ethylene glycol dimethacrylate as the monomers.
Figure 4:
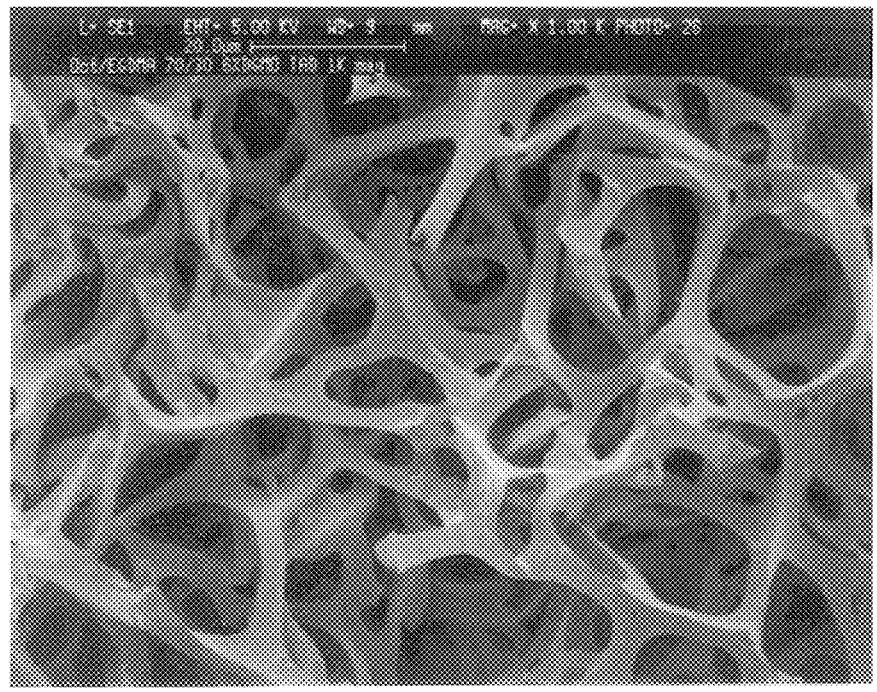
FIG. 4 of the drawings is a photomicrograph (1000× magnification) of the polymeric foam shown in FIG. 3.
Figure 5:
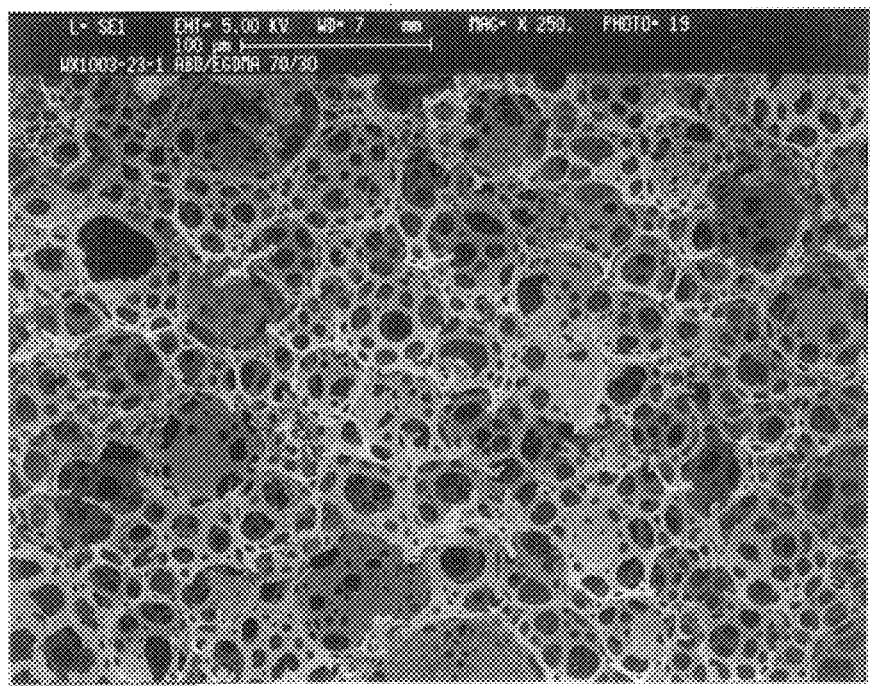
FIG. 5 of the drawings is a photomicrograph (250× magnification) of a section of a polymeric foam made according to the present invention in its expanded state using 2-amyl-1,3-butadiene and ethylene glycol dimethacrylate as the monomers.
Figure 6:
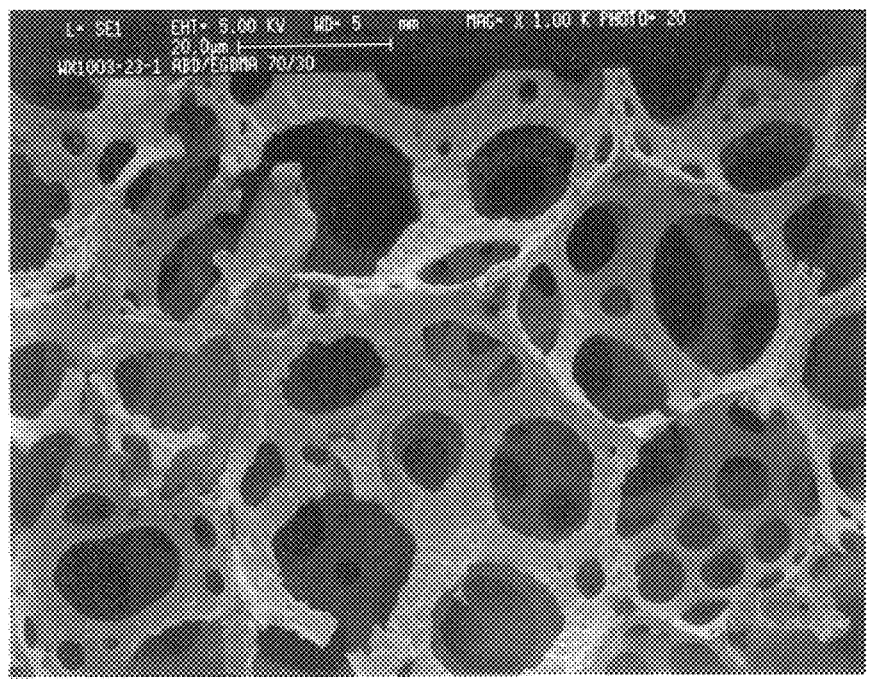
FIG. 6 of the drawings is a photomicrograph (1000× magnification) of the polymeric foam shown in FIG. 5.

The cellular structure of a representative collapsed HIPE foam from which water has been expressed by compression is shown in the photomicrographs of FIGS. 3 and 4. As shown in FIGS. 3 and 4, the cellular structure of the foam is distorted, especially when compared to the HIPE foam structure shown in FIGS. 1 and 2. (The foam structure shown in FIGS. 1 and 2 is in its expanded state.) As can also be seen in FIGS. 3 and 4, the voids or pores (dark areas) in the foam structure have been flattened or elongated.

After compression, and/or thermal drying/vacuum dewatering to a practicable extent, these polymeric foams have residual water that includes both the water of hydration associated with the hydroscopic, hydrated salt incorporated therein, as well as free water absorbed within the foam. It is this residual water (assisted by the hydrated salts) that is believed to exert capillary pressures on the resulting collapsed foam structure. Collapsed polymeric foams of the present invention can have residual water contents of at least about 4%, typically from about 4 to about 30%, by weight of the foam when stored at ambient conditions of 72° F. (22° C.) and 50% relative humidity. Preferred collapsed polymeric foams have residual water contents of from about 5 to about 15% by weight of the foam.

In its collapsed state, the capillary pressures developed within the foam structure at least equal the forces exerted by the elastic recovery or modulus of the compressed polymer. The elastic recovery tendency of polymeric foams can be determined from stress-strain experiments where the expanded foam is compressed to about 25% of its original, expanded caliper (thickness) and then held in this compressed state until an equilibrium or relaxed stress value is measured. For the purposes of the present invention, the equilibrium relaxed stress value is determined from measurements on the polymeric foam in its collapsed state when in contact with aqueous fluids, e.g., water and is hereafter referred to as the "expansion pressure" of the foam. A detailed description of a procedure for determining the expansion pressure of foams is set forth in the TEST METHODS section of copending U.S. application Ser. No. 07/989,270 (Dyer et al), filed Dec. 11, 1992, which is incorporated by reference. The expansion pressure for collapsed polymeric foams of the present invention is about 30 kiloPascals (kPa) or less and typically from about 7 to about 20 kPa, i.e. the expansion pressure is within a relatively narrow range.

It has been found that the specific surface area per foam volume is particularly useful for empirically defining foam structures that will remain in a collapsed state. See copending U.S. application Ser. No. 07/989,270 (Dyer et al), filed Dec. 11, 1992, which is incorporated by reference, where specific area per foam volume is discussed in detail. As used herein, "specific surface area per foam volume" refers to the capillary suction specific surface area of the foam structure times its foam density. Polymeric foams according to the present invention having specific surface area per foam volume values of at least about 0.025 m$^2$/cc, preferably at least about 0.05 m$^2$/cc, most preferably at least about 0.07 m$^2$/cc, have been found empirically to remain in a collapsed state. "Capillary suction specific surface area" is, in general, a measure of the test-liquid-accessible surface area of the polymeric network forming a particular foam per unit mass of the bulk foam material (polymer structural material plus solid residual material). The capillary suction specific surface area is a key feature that influences the capillarity (or capillary absorption pressure) exhibited by an open-celled foam, including those of the present invention. For purposes of this invention, capillary suction specific surface area is determined by measuring the amount of capillary absorption of a low surface tension liquid (e.g., ethanol) which occurs within a foam sample of a known mass and dimensions. A detailed description of such a procedure for determining foam specific surface area via the capillary suction method is set forth in the TEST METHODS section of copending U.S. patent application Ser. No 07/989,270 (Dyer et al.), filed Dec. 11, 1992, which is incorporated by reference. Any reasonable alternative method for determining capillary suction specific surface area can also be utilized. The collapsed polymeric foams of the present invention useful as absorbents are those that have a capillary suction specific surface area of at least about 0.3 m$^2$/g. Typically, the capillary suction specific surface area is in the range from about 0.7 to about 8 m$^2$/g, preferably from about 1 to about 7 m$^2$/g, most preferably from about 1.5 to about 6 m$^2$/g.

A feature that can be useful in defining preferred collapsed polymeric foams is cell size. Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

A number of techniques are available for determining the average cell size of foams. The most useful technique involves a simple measurement based on the scanning electron photomicrograph of a foam sample. The cell size measurements given herein are based on the number average cell size of the foam in its expanded state, e.g., as shown in FIG. 1. The foams useful as absorbents for aqueous body fluids in accordance with the present invention will preferably have a number average cell size of about 50 μm or less and typically in the range of from about 5 to about 50 μm. More preferably, the number average cell size will be in the range from about 5 to about 40 μm, most preferably, from about 5 to about 35 μm.

"Foam density" (i.e., in grams of foam per cubic centimeter of foam volume in air) is specified herein on a dry basis. The amount of absorbed aqueous liquid, e.g., residual salts and liquid left in the foam, for example, after HIPE polymerization, washing and/or hydrophilization, is disregarded in calculating and expressing foam density. Foam density does include, however, other residual materials such as emulsifiers present in the polymerized foam. Such residual materials can, in fact, contribute significant mass to the foam material.

Any suitable gravimetric procedure that will provide a determination of mass of solid foam material per unit volume of foam structure can be used to measure foam density. For example, an ASTM gravimetric procedure described more fully in the TEST METHODS section of copending U.S. application Ser. No. 07/989,270 (Dyer et al), filed Dec. 11, 1992 (herein incorporated by reference) is one method that can be employed for density determination. In their expanded state, polymeric foams of the present invention useful as absorbents have dry basis density values in the range of from about 0.01 to about 0.05 g/cc, preferably from about 0.02 to about 0.03 g/cc.

A particularly important property of absorbent foams of the present invention in their expanded state is their density upon saturation with aqueous body fluids, relative to the dry basis density of the absorbent foam in its collapsed state. The density of the expanded foam, relative to its dry basis density in its collapsed (compressed) state, provides a measure of the relative thickness of the foam in its expanded state. This provides a particularly relevant measure of how thin the foam is when expanded and when saturated with aqueous body fluids.

For the purposes of the present invention, the density of the absorbent foams in their expanded state is measured by the procedure described more fully in the Test Methods section of copending U.S. application Ser. No. 07/989,270 (Dyer et al), filed Dec. 11, 1992, which is incorporated by reference. The density of the foam measured in its expanded state (i.e., after being wetted with aqueous fluid) is then related, as a percentage, to the dry basis density of the foam in its collapsed state. The density of the foam in its expanded state can be in the range of from about 10 to about 50% of its dry basis density in its collapsed state, and is preferably in the range of from about 10 to about 30%, most preferably from about 15 to about 25%.

An important mechanical feature of the absorbent polymeric foams of this invention is their strength in their expanded state, as determined by its resistance to compression deflection (RTCD). The RTCD exhibited by the foams herein is a function of the polymer modulus, as well as the density and structure of the foam network. The polymer modulus is, in turn, determined by a) the polymer composition; b) the conditions under which the foam was polymerized (for example, the completeness of polymerization obtained, specifically with respect to crosslinking); and c) the extent to which the polymer is plasticized by residual material, e.g., emulsifiers, left in the foam structure after processing.

To be useful as absorbents in absorbent articles such as diapers, the foams of the present invention must be suitably resistant to deformation or compression by forces encountered in use when such absorbent materials are engaged in the absorption and retention of fluids. Foams which do not possess sufficient foam strength in terms of RTCD may be able to acquire and store acceptable amounts of body fluid under no-load conditions but will too easily give up such fluid under the compressive stress caused by the motion and activity of the user of the absorbent articles that contain the foam.

The RTCD exhibited by the polymeric foams of the present invention can be quantified by determining the amount of strain produced in a sample of saturated foam held under a certain confining pressure for a specified temperature and period of time. The method for carrying out this particular type of test is described hereafter in the TEST METHODS section. The foams useful as absorbents are those which exhibit a resistance to compression deflection such that a confining pressure of 0.74 psi (5.1 kPa) produces a strain of typically from about 2 to about 80% compression of the foam structure when it has been saturated to its free absorbent capacity with synthetic urine having a surface tension of 65±5 dynes/cm. Preferably the strain produced under such conditions will be in the range from about 5 to about 40%, most preferably from about 5 to about 25%.

Suitable absorbent foams will in general exhibit especially desirable and useful body fluid handling and absorbency characteristics. The fluid handling and absorbency characteristics that are most relevant to the realization of suitable absorbent foams are: A) the free absorbent capacity of the foam; B) the rate of vertical wicking of fluid through the foam structure; and C) the absorbent capacity of the foam at specific reference wicking heights.

"Free absorbent capacity" is the total amount of test fluid (synthetic urine) which a given foam sample will absorb into its cellular structure per unit mass of solid material in the sample. To be especially useful in absorbent articles for absorbing urine, the absorbent foams of the present invention should have a free capacity of at least about 12, and preferably at least about 20 mL of synthetic urine per gram of dry foam material. The procedure for determining the free absorbent capacity of the foam is described hereafter in the TEST METHODS section. "Vertical wicking," i.e., fluid wicking in a direction opposite from gravitational force, is an especially desirable performance attribute for absorbent foams herein. This is because such foams will frequently be utilized in absorbent articles in a manner that fluid to be absorbed must be moved within the article from a relatively lower position to a relatively higher position within the absorbent core of the article.

Vertical wicking performance is determined by measuring the time taken for a colored test liquid (e.g., synthetic urine) in a reservoir to wick a vertical distance of 5 cm through a test strip of foam of specified size. The vertical wicking performance procedure is described in greater detail in the TEST METHODS section of copending U.S. application Ser. No. 07/989,270 (Dyer et al), filed Dec. 11, 1992 (herein incorporated by reference), but is performed at 31° C., instead of 37° C. To be especially useful in absorbent articles for absorbing urine, the foam absorbents of the present invention will preferably vertically wick synthetic urine (65±5 dynes/cm) to a height of 5 cm in no more than about 30 minutes. More preferably, the preferred foam absorbents of the present invention will vertically wick synthetic urine to height of 5 cm in no more than about 5 minutes.

The vertical wicking absorbent capacity test measures the amount of test fluid per gram of absorbent foam that is held within each one inch (2.54 cm) vertical section of the same standard size foam sample used in the vertical wicking rate test. Such a determination is generally made after the sample has been allowed to vertically wick test fluid to equilibrium (e.g., after about 18 hours). Like the vertical wicking rate test, the vertical wicking absorbent capacity test is described in greater detail in the TEST METHODS section of copending U.S. application Ser. No. 07/989,270 (Dyer et al), filed Dec. 11, 1992, which is incorporated by reference. To be especially useful in absorbent articles for absorbing urine, the preferred absorbent foams of the present invention will generally have a vertical wicking absorbent capacity such that, at 11.4 cm (4.5 inches) of vertical wicking height, the foam test strip wicks to at least about 50%, most preferably at about 75%, of its free absorbent capacity.

D. Uses of Polymers

1. In general

Polymers according to the present invention are broadly useful in a variety of applications, including packaging wraps, insulating cup and food containers used in the fast food industry, microwave dinner containers (plates, utensils, etc.), disposable diaper backsheets, binders for nonwovens, paints, agricultural films and coverings, and the like.

2. Latexes

Latexes according to the present invention can be used in a myriad of commercial products and applications where emulsions of this general type are employed. *Encyclopedia of Polymer Science and Engineering*, Vol. 8, (Second Edition Wiley & Sons, New York, N.Y., 1988), p 647. Representative examples include nonwovens where latexes are used as binders; paper where latexes are used as coatings; adhesive applications; and the like. Latexes according to the present invention can also be processed into the form of a film by the addition of a coagulant and/or removal of water.

In general, any application where a coating or a binder is desired would be suitable for latexes according to the present invention. For example, a paper substrate can be coated with the latex by spraying, dipping or other means so as to produce a stronger, water-proof fiber-reinforced film. If the latex is formed using a cationic surfactant (or if a cationic retention aid is used), the latex can be incorporated into the paper web by wet end addition during the forming process. The dried paper reinforced with latex forms a product useful in coated paper applications. Latex adhesives according to the present invention can provide bonding of substrates and materials.

Latex binders according to present invention can also be formulated from "latent crosslinkers," typically combinations of an aldehyde with an amide, as exemplified by N-methylolacrylamide (NMA). "Latent crosslinkers" such as NMA crosslink the latex polymer during drying or water removal. Accordingly, the latexes of the present invention can be made as an uncrosslinked copolymer from, for example, 1,3,7-octatriene and NMA. Upon drying , the NMA reacts to form crosslinks required for strength purposes, among other properties.

3. Uses of Polymeric Foams, including HIPE Foams a. In General

Polymers according to the present invention prepared as open-celled foams are also broadly useful. In particular, these open-celled polymeric foams can be employed as absorbent cores in disposable diapers, as well as other absorbent articles. These open-celled foams can also be employed as environmental waste oil sorbents; as absorbent components in bandages or dressings; to apply paint to various surfaces; in dust mop heads; in wet mop heads; in dispensers of fluids; in packaging; in odor/moisture sorbents; in cushions; in gloves, and for many other uses.

b. Absorbent Articles

The polymeric foams of the present invention can also be used as at least a portion of the absorbent structures (e.g., absorbent cores) for various absorbent articles. By "absorbent article" herein is meant a consumer product that is capable of absorbing significant quantities of urine or other fluids (i.e., liquids), like aqueous fecal matter (runny bowel movements), discharged by an incontinent wearer. Examples of such absorbent articles include disposable diapers, incontinence garments and pads, catamenials such as tampons and sanitary napkins, disposable training pants, bed pads, clothing shields, and the like.

In its simplest form, an absorbent article of the present invention need only include a backing sheet, typically relatively liquid-impervious, and one or more absorbent foam structures associated with this backing sheet. The absorbent foam structure and the backing sheet will be associated in such a manner that the absorbent foam structure is situated between the backing sheet and the fluid discharge region of the wearer of the absorbent article. Liquid impervious backing sheets can comprise any material, for example polyethylene or polypropylene which will help retain fluid within the absorbent article.

More conventionally, the absorbent articles herein will also include a liquid-pervious topsheet element that covers the side of the absorbent article that touches the skin of the wearer. In this configuration, the article includes an absorbent core comprising one or more absorbent foam structures of the present invention positioned between the backing sheet and the topsheet. Liquid-pervious topsheets can comprise any material such as polyester, polyolefin, rayon and the like that is substantially porous and permits body fluid to readily pass there through and into the underlying absorbent core. The topsheet material will preferably have no propensity for holding aqueous body fluids in the area of contact between the topsheet and the wearer's skin.

The absorbent core of the absorbent article embodiments of this invention can consist solely of one or more of the foam structures herein. For example, the absorbent core can comprise a single unitary piece of foam shaped as desired or needed to best fit the type of absorbent article in which it is to be used. Alternatively, the absorbent core can comprise a plurality of foam pieces or particles that can be adhesively bonded together or which can simply be constrained into an unbonded aggregate held together by means of the topsheet and backing sheet of the absorbent article.

The absorbent core of the absorbent articles herein can also comprise other conventional, elements or materials in addition to one or more absorbent foam structures of the present invention. For example, absorbent articles herein can utilize an absorbent core that comprises a combination, e.g., an air-laid mixture, of particles or pieces of the absorbent foam structures herein and conventional absorbent materials such as wood pulp or other cellulosic fibers, as well as particles or fibers of hydrogel-forming absorbent polymers.

In one embodiment involving a combination of the absorbent foam herein and other absorbent materials, the absorbent articles herein can employ a multi-layer absorbent core configuration wherein a core layer containing one or more foam structures of this invention can be used in combination with one or more additional separate core layers comprising conventional absorbent structures or materials. Such conventional absorbent structures or materials, for example, can include air-laid or wet-laid webs of wood pulp or other cellulosic fibers. Such conventional structures can also comprise conventional, e.g., large cell, absorbent foams or even sponges. The conventional absorbent structures used with the absorbent foam herein can also contain, for example up to 80% by weight, of particles or fibers of hydrogel-forming absorbent polymers of the type commonly used in absorbent articles that are to acquire and retain aqueous body fluids. Hydrogel-forming absorbent polymers of this type and their use in absorbent articles are more filly described in U.S. Reissue Patent 32,649 (Brandt et al), reissued Apr. 19, 1988, which is incorporated by reference.

One preferred type of absorbent article herein is one that utilizes a multi-layer absorbent core having fluid handling layer positioned in the fluid discharge region of the wearer of the article. This fluid-handling layer can be in the form of a high loft nonwoven, but is preferably in the form of a fluid acquisition/distribution layer comprising a layer of modified cellulosic fibers, e.g., stiffened curled cellulosic fibers, and optionally up to about 10% by weight of this fluid acquisition/distribution layer of polymeric gelling agent. The modified cellulosic fibers used in the fluid acquisition/distribution layer of such a preferred absorbent article are preferably wood pulp fibers that have been stiffened and curled by means of chemical and/or thermal treatment. Such modified cellulosic fibers are of the same type as are employed in the absorbent articles described in U.S. Pat. No. 4,935,622 (Lash et al), issued Jun. 19, 1990, which is incorporated by reference.

These multi-layer absorbent cores also comprise a second lower, fluid storage/redistribution layer comprising a foam structure of the present invention. For purposes of this invention, an "upper" layer of a multi-layer absorbent core is a layer that is relatively closer to the body of the wearer, e.g., the layer closest to the article topsheet. The term "lower" layer conversely means a layer of a multi-layer absorbent core that is relatively further away from the body of the wearer, e.g., the layer closest to the article backsheet. This lower fluid storage/redistribution layer is typically positioned within the absorbent core so as to underlie the (upper) fluid-handling layer and be in fluid communication therewith. Absorbent articles that can utilize the absorbent foam structures of this invention in a lower fluid storage/redistribution layer underlying an upper fluid acquisition/distribution layer containing stiffened curled cellulosic fibers are described in greater detail in the U.S. Pat. No. 5,147,345 (Young et al), issued Sep. 15, 1992 which is incorporated by reference.

As indicated hereinbefore, the fluid handling and mechanical characteristics of the specific absorbent foam structures herein render such structures especially suitable for use in absorbent articles in the form of disposable diapers. Disposable diapers comprising the absorbent foam structures of the present invention can be made by using conventional diaper making techniques, but by replacing or supplementing the wood pulp fiber web ("airfelt") or modified cellulosic core absorbents typically used in conventional diapers with one or more foam structures of the present invention. Foam structures of this invention can thus be used in diapers in single layer or, as noted hereinbefore, in various multiple layer core configurations. Articles in the form of disposable diapers are more fully described in U.S. Reissue Patent 26,151 (Duncan et al), reissued Jan. 31, 1967; U.S. Pat. No. 3,592,194 (Duncan), issued Jul. 13, 1971; U.S. Pat. No. 3,489,148 (Duncan et al), issued Jan. 13, 1970; U.S. Pat. No. 3,860,003, issued Jan. 14, 1975; and U.S. Pat. No. 4,834,735 (Alemany et al), issued May 30, 1989; all of which are incorporated by reference.

Figure 7:
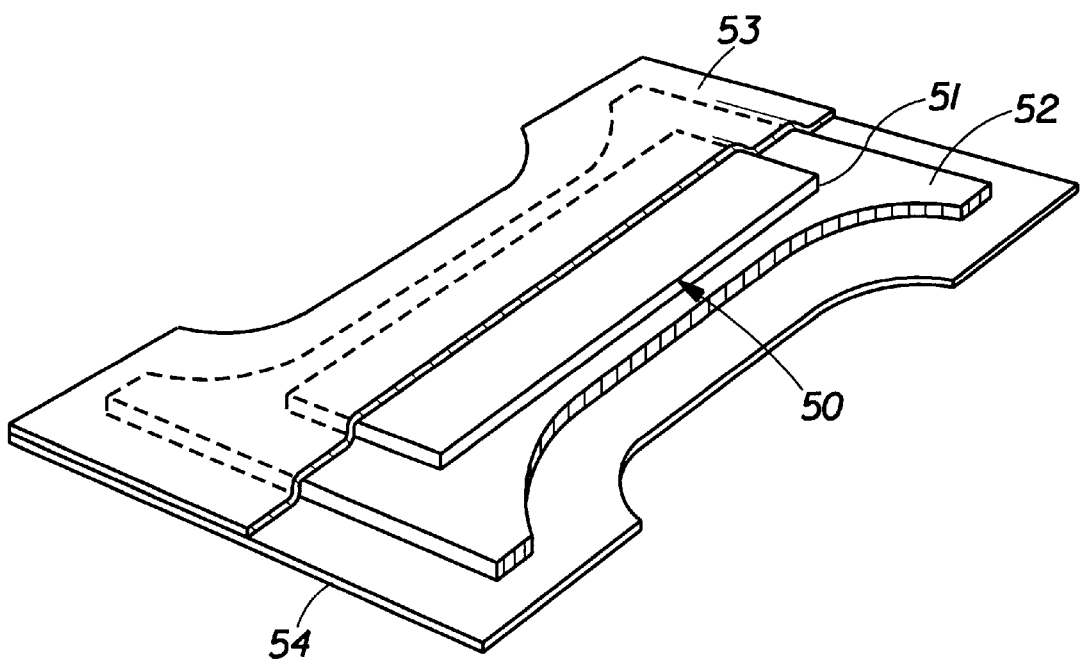
FIG. 7 of the drawings is a cutaway depiction of a disposable diaper that utilizes the absorbent polymeric foam of the present invention as an hourglass-shaped fluid storage/distribution component in an absorbent diaper core of dual-layer configuration.

One such disposable diaper embodiment according to the present invention is illustrated by FIG. 7 of the drawings. Such a diaper includes an absorbent core 50, comprising an upper fluid acquisition layer 51, and an underlying fluid storage/distribution layer 52 comprising an absorbent foam structure of this invention. A topsheet 53 is superposed and co-extensive with one face of the core, and a liquid impervious backsheet 54 is superposed and coextensive with the face of the core opposite the face covered by the topsheet. The backsheet most preferably has a width greater than that of the core thereby providing side marginal portions of the backsheet which extend beyond the core. The diaper is preferably constructed in an hourglass configuration.

Another type of absorbent article which can utilize the absorbent foam structures of the present invention comprises form-fitting products such as training pants. Such form-fitting articles will generally include a nonwoven, flexible substrate fashioned into a chassis in the form of briefs or shorts. An absorbent foam structure according to the present invention can then be affixed in the crotch area of such a chassis in order to serve as an absorbent "core". This absorbent core will frequently be over-wrapped with envelope tissue or other liquid pervious, nonwoven material. Such core overwrapping thus serves as the "topsheet" for the form-fitting absorbent article.

The flexible substrate which forms the chassis of the form-fitting article can comprise cloth or paper or other kinds of nonwoven substrate or formed films and can be elasticized or otherwise stretchable. Leg bands or waist bands of such training pants articles can be elasticized in conventional fashion to improve fit of the article. Such a substrate will generally be rendered relatively liquid-impervious, or at least not readily liquid-pervious, by treating or coating one surface thereof or by laminating this flexible substrate with another relatively liquid-impervious substrate to thereby render the total chassis relatively liquid-impervious. In this instance, the chassis itself serves as the "backsheet" for the form-fitting article. Typical training pants products of this kind are described in U.S. Pat. No. 4,619,649 (Roberts), issued Oct. 28, 1986, which is incorporated by reference.

Figure 8:
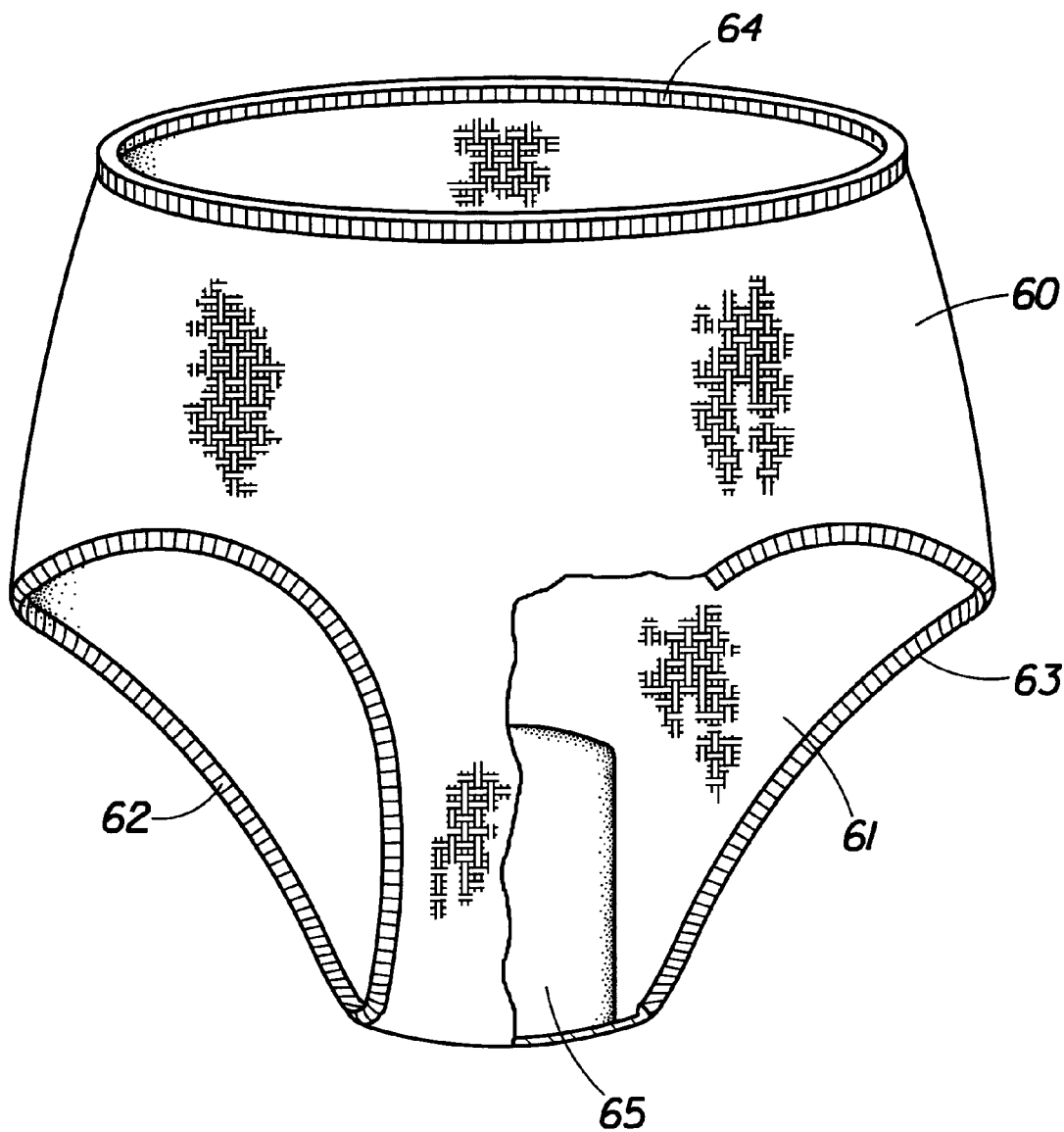
FIG. 8 of the drawings represents a cut-away view of a form-fitting article such as a disposable training pants product that employs an absorbent polymeric foam according to the present invention as an absorbent core.

A typical form-fitting article in the form of a disposable training pants product is shown in FIG. 8 of the drawings. Such a product comprises an outer layer 60 affixed to a lining layer 61 by adhesion along the peripheral zones thereof. For example, the inner lining 61 can be affixed to the outer layer 60, along the periphery of one leg band area 62, along the periphery of the other leg band area 63, and along the periphery of waistband area 64. Affixed to the crotch area of the article is a generally rectangular absorbent core 65 comprising an absorbent foam structure of the present invention.

E. Test Methods

1. Resistance to Compression Deflection (RTCD)

Resistance to compression deflection can be quantified by measuring the amount of strain (% reduction in thickness) produced in a foam sample which has been saturated and expanded with synthetic urine, after a confining pressure of 0.74 psi (5.1 kPa) has been applied to the sample.

Jayco synthetic urine used in this method is prepared by dissolving a mixture of 2.0 g KCl, 2.0 g $Na_2SO_4$, 0.85 g $NH_4H_2PO_4$, 0.15 g $(NH_4)_2HPO_4$, 0.19 g $CaCl_2$, and 0.23 g $MgCl_2$ to 1.0 liters with distilled water. The salt mixture can be purchased from Endovations, Reading, Pa (cat No. JA-00131-000-01).

The foam samples, Jayco synthetic urine and equipment used to make measurements are all equilibrated to a temperature of 31° C. All measurements are also performed at this temperature.

A foam sample sheet in its collapsed state is expanded and saturated to its free absorbent capacity by soaking in a bath of Jayco synthetic urine. After 3 minutes, a cylinder having a 1 $in^2$ (6.5 $cm^2$) circular surface area is cut out of the saturated, expanded sheet with a sharp circular die. The cylindrical sample is soaked in synthetic urine at 31° C. for a further 6 minutes. The sample is then removed from the synthetic urine and is placed on a flat granite base under a gauge suitable for measuring the sample thickness. The gauge is set to exert a pressure of 0.08 psi on the sample. Any gauge fitted with a foot having a circular surface area of at least 1 $in^2$ (6.5 $cm^2$) and capable of measuring thickness to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan).

After 2 to 3 min., the expanded thickness (X1) is recorded. A force is then applied to the foot so that the saturated foam sample is subjected to a pressure of 0.74 psi (5.1 kPa) for 15 minutes. At the end of this time, the gauge is used to measure the final sample thickness (X2). From the initial and final thickness measurements, the percent strain induced can be calculated for the sample as follows: $[(X1-X2)/X1] \times 100 = \%$ reduction in thickness.

2. Free Absorbent Capacity

Free absorbent capacity can be quantified by measuring the amount synthetic urine absorbed in a foam sample which has been saturated and expanded with synthetic urine.

The foam samples and Jayco synthetic urine are equilibrated to a temperature of 31° C. Measurements are performed at ambient temperature.

A foam sample sheet in its collapsed state is expanded and saturated to its free absorbent capacity by soaking in a bath of Jayco synthetic urine. After 3 minutes, a cylinder having a 1 $in^2$ (6.5 $cm^2$) circular surface area is cut out of the saturated, expanded sheet with a sharp circular die. The cylindrical sample is soaked in synthetic urine at 31° C. for a further 3 minutes. The sample is then removed from the synthetic urine and is placed on a digital balance. Any balance fitted with a weighing pan having an area larger than that of the sample and with a resolution of 1 milligram or less can be employed. Examples of such balances are the Mettler PM 480 and Mettler PC 440 (Mettler Instrument Corp; Hightstown N.J.).

After determining the weight of the wet foam sample (Ww), it is placed between 2 fine plastic mesh screens on top of 4 disposable paper towels. The sample is squeezed 3 times by firmly rolling a plastic roller over the top screen. The sample is then removed, soaked in distilled water for approximately 2 minutes, and squeezed between mesh screens as before. It is then placed between 8 layers of disposable paper towels (4 on each side) and pressed with 20,000 lbs. of force in a Carver Laboratory Press. The sample is then removed from the paper towels, dried in a Fisher convection oven at 82° C. for 20 minutes, and its dry weight recorded (Wd).

The free absorbent capacity (FAC) is the wet weight (Ww), less the dry weight (Wd) divided by the dry weight (Wd), i.e., $FAC=[(Ww-Wd)/Wd]$

SPECIFIC EXAMPLES

The following are specific examples of HIPE foams and other polymer forms prepared according to the present invention:

Example 1: Preparation of HIPE Foam

A HIPE is prepared from an oil phase consisting of 7.0 g 1,3,7-octatriene, 3.0 g ethylene glycol dimethacrylate, 0.05 g Tinuvin 765, and 0.6 g polyglycerol ether emulsifier comprising primarily diglycerol ethers of coconut fatty alcohols. To this is added an aqueous solution consisting of 300 mL water containing 3.0 g calcium chloride (anhydrous) and 0.45 g potassium persulfate in rapid dropwise fashion with stirring using a 4 prong flat-bladed paddle at 300 rpm. The addition takes approximately 5–7 minutes and results in a white creamy emulsion. The emulsion container is capped and placed in an oven set at 65° C. for 48 hrs. The container is then cut away from the water-logged foam. The foam can then be sliced and dewatered by a combination of pressure and heat resulting in a dry porous open-celled foam having a density of approximately 30 mg/cc in its expanded state.

Example 2: Preparation of HIPE Foams

The procedure of Example 1 is generally used in preparing foams with the following crosslinking agents substituted for ethylene glycol dimethacrylate: (2a) trimethylolpropane dimethacrylate; (2b) 1,6-hexanediol diacrylate; (2c) 1,4-butanediol dimethacrylate; (2d) 2-butene-1,4-diol dimethacrylate; (2e) diethylene glycol dimethacrylate. Following curing and dewatering, open-celled porous foams having a density of approximately 30 mg/cc are obtained.

Example 3. Preparation of HIPE Foams

The procedure of Example 1 is generally used in preparing foams with the following polyenes being substituted for 1,3,7-octatriene: (3a) 1,3-octadiene; (3b) 2,3-dimethylbutadiene (cure temperature reduced to 50° C.); (3c) 1,3-hexadiene; (3d) 2-amylbutadiene; (3d) β-myrcene. Following curing and dewatering, open-celled porous foams having a density of approximately 30 mg/cc are obtained. The glass transition temperatures (Tg) of some representative foams are shown in Table 1 below:

TABLE 1

| Sample | Polyene (wt. %) | Crosslinker (wt. %) | Adjuvant (wt. %) | Tg (° C.) |
|---|---|---|---|---|
| 1 | 1,3,7-octatriene (65%) | DEGDMA (35%) | none | 28 |
| 2 | 1,3,7-octatriene (60%) | DEGDMA (40%) | none | 40 |
| 3 | 1,3,7-octatriene (70%) | EGDMA (30%) | none | 53 |
| 4 | 1,3,7-octatriene (80%) | EGDMA (20%) | none | 15 |
| 5 | 1,3,7-octatriene (65%) | EGDMA (20%) | MMA (15%) | 32 |
| 6 | 1,3,7-octatriene (60%) | EGDMA (30%) | EHA (10%) | 41 |
| 7 | 1,3,7-octatriene (58%) | EGDMA (32%) | DOS (10%) | 20 |
| 8 | 1,3,7-octatriene (75%) | TMPTMA (25%) | none | 46 |
| 9 | 2,3-DMB (75%) | EGDA (25%) | none | 71 |
| 10 | 2,3-DMB (70%) | EGDA (30%) | none | 67 |
| 11 | 2,3-DMB (80%) | TMPTA (20%) | none | 54 |

DEGDMA = diethylene glycol dimethacrylate
EGDMA = ethylene glycol dimethacrylate
MMA = methyl methacrylate
EHA = 2-ethyl hexyl acrylate
DOS = dioctyl sebacate
TMPTMA = trimethylolpropane trimethacrylate
EGDA = ethylene glycol diacrylate
TMPTA = trimethylolpropane triacrylate
2,3-DMB = 2,3-dimethyl-1,3-butadiene Tg values are determined using samples cut to 25 mm diameter ca. 5 mm thick parallel plate compression mode using a Rheometrics RSA2 dynamic analyzer. Instrument parameters are set at 0.1% dynamic strain, 1 d dynamic frequency, 20–50 g static force autotension, sweeping from to about −50° C. to about 100° C. in 2.5° C. increments with a soak time of 125 seconds. The Tg value is taken as the peak in the tan[δ] curve in the temperature sweep.

Example 4: Preparation of Foam from a HIPE.

To a 300 mL polyethylene bottle is added 5 g of an oil phase containing 70 parts by weight of 2-amylbutadiene, 15 parts divinylbenzene (55% pure), 15 parts trimethylopropane triacrylate, and 15 parts SPAN® 20 emulsifying agent. The contents are stirred with a Teflon-coated paint-stirrer at 200 rpm. An aqueous phase (150 g) containing 90 parts by weight of water, 10 parts calcium chloride, and 0.15 parts potassium persulfate is added dropwise over a period of 15 min. The resulting emulsion is poured into a polyethylene container and cured in an oven at 65° C. for 48 hours. After dewatering, the resulting foam has an absorbency of 29.6 g of water per gram of dry foam.

Example 5: Preparation of HIPE Foam

To a 600 mL polyethylene bottle is added 10 g of an oil phase containing amounts in parts by weight of 1,3,7-octatriene (OT), trimethylolpropane trimethacrylate (TMPTMA), and antioxidant (Irganox 1076 [octadecyl 3,5-di-t-butyl-4-hydroxyhydrocinnanate] or Tinuvin 765 [bis(1,2,2,6,6-pentamethyl-4-piperidinyl)sebacate as major component]as listed in the Table 2 below, and 9 parts of cocoyl diglycerol ether. The contents are stirred with a Teflon-coated spashless paint stirrer by an overhead stirring motor at a speed of 200 rpm. An aqueous phase (300 g) containing 90 parts by weight of water, 10 parts of calcium chloride, and 0.15 parts of potassium persulfate is added dropwise over a period of about 30 minutes. The resulting creamy white emulsions are poured into polyethylene containers and cured in a forced air oven at 65° C. for 48 hours. The properties of the resulting foams after dewatering are listed in Table 2 below:

TABLE 2

| OT/TMPTMA | Antioxidant | % Free Water | Buckling Stress (psi) |
|---|---|---|---|
| 70/30 | None | 4.1 | 5.1 |
| 70/30 | 0.5% Tinuvin | 4.0 | 5.0 |
| 70/30 | 1.0% Tinuvin | 4.8 | 6.1 |
| 70/30 | 0.5% Irganox | 4.8 | 5.2 |
| 75/25 | None | 7.3 | 0.42 |
| 75/25 | 1.0% Tinuvin | 5.8 | 1.05 |
| 75/25 | 0.5% Irganox | 6.9 | 0.26 |
| 75/25 | 0.2% Irganox + 0.8% Irgaphox 168 | 6.8 | 0.29 |
| 75/25 | 0.3% Irganox + 0.6% DSTDP | 7.3 | 0.26 |

As can be seen in Table 2 above, the presence of antioxidants in the oil phase has no effect on curing as measured by the amount of free water after curing. At lower crosslinker concentrations, foam properties appear to be sensitive to the nature of the antioxidant. Tinuvin gives a stronger foam than conventional antioxidants.

Example 6: Effect of Antioxidants on HIPE Foam

The effect of hindered phenol antioxidants against oxidative degradation of the foam is tested on the following HIPE formulations: A HIPE is prepared with an oil phase containing 70 parts of 1,3,7-octatriene (OT), 30 parts ethylene glycol dimethacrylate (EGDMA), and 6 parts cocoyl diglycerol ether emulsifier; and a water phase containing 10% calcium chloride and 0.15% potassium persulfate. A second HIPE is made using the same monomer formulation but with 0.1 parts of an antioxidant (Irganox 1076) in the oil phase. The HIPEs are prepared by adding the water phase to the oil phase at a water:oil ratio of 30:1 and then stirring this mixture with a splashless paint mixer at 200 rpm. The HIPEs are cured at 65° C. for 48 hours. After curing, each HIPE foam is sliced and washed twice with water and squeezed to remove excess fluid. Approximately 6–7 grams of moist foam is weighed into a headspace vial and capped with a crimp top. Total ion chromatograms of the headspace components of each foam are determined after the samples are equilibrated for one hour at 100° C. Analysis shows the presence of acrolein, an oxygenate, in the vapor phase. The amount of acrolein decreased significantly, close to the detection limit, for the HIPE foam containing the antioxidant.

Example 7: Preparation of a Multiple-Armed Polydiene.

A multiple-armed polydiene is prepared by anionic polymerization of 2,3-dimethylbutadiene followed by coupling with ethylene glycol dimethacrylate as follows: To a 250 mL glass bottle in an oxygen and moisture-free chamber is added 10 g of 2,3-dimethylbutadiene, 100 mL of cyclohexane, and 5.1 g of diethyl ether. The resulting mixture is titrated with 1.3M sec-butyl lithium solution in cyclohexane until a persistent yellow color is obtained. An additional 1.22 mmol of sec-butyl lithium is added as initiator. After 72 hr at room temperature, the polymer solution is treated with 0.5 g of ethylene glycol dimethacrylate and stirred for an additional 48 hr prior to termination with 1 mL of methanol. Removal of solvent by rotary evaporation and further drying in a vacuum oven to constant weight yields 8.51 g of a white solid. A 20% by weight solution of the polymer in cyclohexane has a room temperature viscosity of 69 centipoise.

Example 8: HIPE Foams Made by Continuous Process

HIPE foams are prepared generally according to the continuous process described in U.S. Pat. No. 5,149,720. The monomer formulations used in the HIPEs, as well as the processing conditions used to prepare the HIPEs and the resulting foams, are shown in Table 3 below:

TABLE 3

| Sample | OCT | EGDMA | EHA | DOS | W:O Ratio | Pour Temp. (° F.) | Impeller (rpm) |
|---|---|---|---|---|---|---|---|
| 1 | 60% | 30% | 10% | — | 30.2 | 110° | 900 |
| 2 | 60% | 30% | 10% | — | 29.9 | 89 | 600 |
| 3 | 60% | 30% | 10% | — | 30.0 | 89 | 500 |
| 4 | 58% | 32% | — | 10% | 35.2 | 111 | 1200 |
| 5 | 58% | 32% | — | 10% | 30.4 | 116 | 1200 |
| 6 | 58% | 32% | — | 10% | 35.3 | 117 | 1200 |
| 7 | 58% | 32% | — | 10% | 40.3 | 116 | 1200 |

OCT = 1,3,7-octatriene
EGDMA = ethylene glycol dimethacrylate
EHA = 2-ethyl hexyl acrylate
DOS = dioctyl sebacate Each HIPE is prepared with 0.5% Tinuvin 765 antioxidant and 6% cocoyl diglycerol ether emulsifier in the oil phase and 10% calcium chloride and 0.15% potassium persulfate in the water phase. The properties of the resultant HIPE foams are shown in Table 4 below:

TABLE 4

| Sample | Collapsed Thickness (in) | Expanded Thickness (in) | Expansion Factor* | FAC** | % RTCD*** |
|---|---|---|---|---|---|
| 1 | .031 | .144 | 4.6 | 31.4 | 6.3% |
| 2 | .032 | .138 | 4.3 | 28.9 | 7.2% |
| 3 | .034 | .142 | 4.2 | 29.1 | 4.2% |
| 4 | .040 | .140 | 3.5 | 28.5 | 4.1% |
| 5 | .034 | .145 | 4.3 | 26.0 | 12.2% |
| 6 | .029 | .150 | 4.4 | 31.2 | 23.0% |
| 7 | .022 | .118 | 5.4 | 36.2 | 21.7% |

*Ratio of expanded to collapsed thickness
**FAC = Free Absorbent Capacity
**RTCD = Resistance to Compression Deflection (0.74 psi load for 15 minutes at 31° C.)

Example 9: Diaper Made with HIPE Foam

Figure 9:
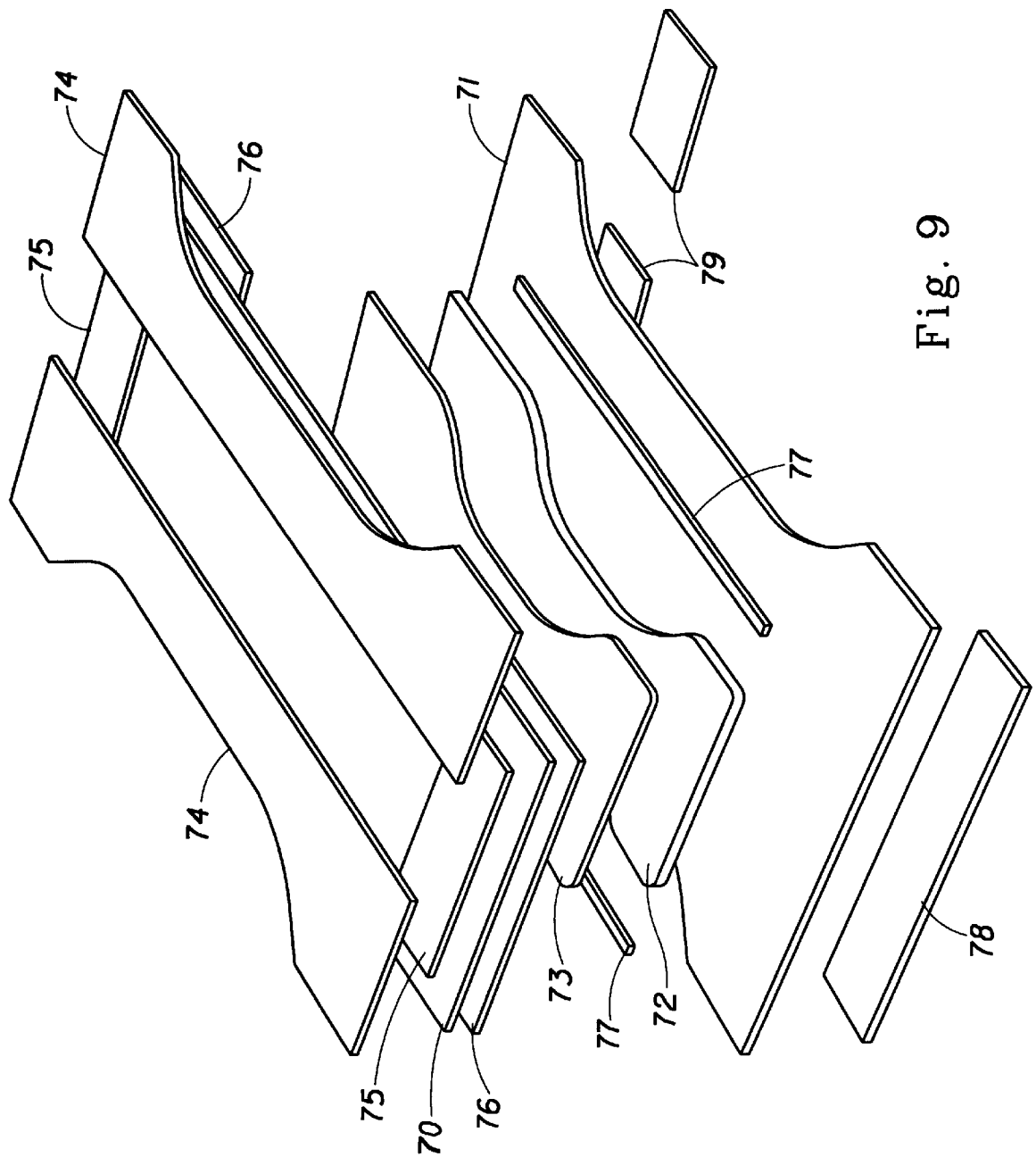
FIG. 9 of the drawings represents a blown-apart view of the components of a diaper structure also of dual layer core configuration having an hourglass-shaped fluid acquisition layer overlying an absorbent foam fluid storage/distribution layer with a modified hourglass shape.

A disposable diaper is prepared using the configuration and components shown in expanded and blown-apart depiction in FIG. 9. Such a diaper comprises a topsheet 70, a fluid-impervious backsheet 71, and a dual layer absorbent core positioned between the topsheet and the backing sheet. The dual layer absorbent core comprises a modified hourglass-shaped, fluid storage/redistribution layer 72 comprising the collapsed HIPE foams according to Examples 1, 2 or 3 positioned below a modified-hourglass shaped fluid acquisition layer 73. The topsheet contains two substantially parallel barrier leg cuff strips 74 with elastic. Affixed to the diaper backsheet are two rectangular elasticized waistband members 75. Also affixed to each end of the backsheet 71 are two waistshield elements 76 constructed of polyethylene. Also affixed to the backsheet are two parallel leg elastic strips 77. A sheet of polyethylene 78 is affixed to the outside of the backsheet as a dedicated fastening surface for two pieces 79 of Y-tape which can be used to fasten the diaper around the wearer.

The acquisition layer of the diaper core comprises a 92%/8% wet-laid mixture of stiffened, twisted, curled cellulosic fibers and conventional non-stiffened cellulosic fibers. The stiffened, twisted, curled cellulosic fibers are made from southern softwood kraft pulp (Foley fluff) which has been crosslinked with glutaraldehyde to the extent of about 2.5 mole percent on a dry fiber cellulose anhydroglucose basis. The fibers are crosslinked according to the "dry crosslinking process" as described in U.S. Pat. No. 4,822,453 (Dean et al), issued Apr. 18, 1989.

These stiffened fibers are similar to the fibers having the characteristics described as follows in Table 5:

TABLE 5

Stiffened, Twisted, Curled Cellulose (STCC) Fibers

Type=Southern softwood kraft pulp crosslinked with glutaraldehyde to the extent of 1.41 mole percent on a dry fiber cellulose anhydroglucose basis Twist Count Dry=6.8 nodes/mm Twist Count Wet=5.1 nodes/m 2-Propanol Retention Value=24%

Water Retention Value=37%

Curl Factor=0.63

The conventional non-stiffened cellulose fibers used in combination with the STCC fibers are also made from Foley fluff. These non-stiffened cellulose fibers are refined to about 200 CSF (Canadian Standard Freeness).

The acquisition layer has an average dry density of about 0.01 g/cc, an average density upon saturation with synthetic urine, dry weight basis, of about 0.08 g/cc, and an average basis weight of about 0.03 g/cc. About 8 grams of the fluid acquisition layer are used in the diaper core. The surface area of the acquisition layer is about 46.8 in$^2$ (302 cm$^2$). It has a caliper of about 0.44 cm.

The fluid storage/redistribution layer of the diaper core comprises a modified hourglass shaped piece of collapsed HIPE foam of the type described in Examples 1, 2 or 3. About 8 grams of HIPE foam are used to form this storage/distribution layer which has a surface area of about 52.5 in$^2$ (339 cm$^2$) and a caliper of about 0.1 in (0.25 cm).

If desired, air-laid stiffened fibers are substituted for the wet-laid stiffened fibers in the acquisition layer of the absorbent core.

Example 10: Preparation of Latex

A latex is prepared in the following manner: A monomer solution of 28.0 g of 1,3,7-octatriene, 12.0 g of ethylene glycol dimethacrylate, and 0.2 g of Tinuvin 765 is prepared at room temperature. A 50 mL aqueous solution containing 5 g of dodecylbenzenesulfonic acid, sodium salt and 0.1 g of potassium persulfate is prepared separately and transferred to a 100 mL resin kettle equipped with a magnetic stirrer, condenser, addition funnel and a thermometer. The kettle is heated in an oil bath until the internal temperature is about 85° C. The monomer solution is then added dropwise with stirring over a period of ca. 1 hr. to form a milky white emulsion. After 37 g of the monomer solution has been added, a mild exotherm is observed and the temperature rises to approximately 90° C. The mixture begins to boil and the addition of monomer is stopped. The mixture is allowed to stir at 86° C. for ca. 1 hr. and allowed to cool. The emulsion is then filtered through a nylon screen (0.5 mm mesh) to remove a small amount of coagulum. The emulsion is placed in an oven at 65° C. for ca. 1 hr. to ensure complete polymerization.

The resulting latex is coated onto a number of surfaces, and allowed to dry. Clear transparent films are formed on smooth glass and aluminum substrates. A tough flexible glossy film is obtained by coating a piece of white printer paper. The latex is also used as an adhesive between two plastic weigh boats, and between two painted metal lids. Impregnating tissue paper with the latex yields a translucent thin film on drying.

Example 11: Wet-End Addition of Latex

A 1 square foot handsheet is prepared using 2.5 g unrefined bleached Northern softwood Kraft cellulose fiber using a deckle box containing 6 gal water. The fiber is suspended in the water in the deckle box, the pH is adjusted to near 8, and Kymene 557 H resin (Hercules) is added (1% on an active basis by weight of pulp fiber). The suspension is agitated for 5 minutes to allow deposition of the resin onto the pulp fibers. The latex of Example 10 is then added (10% on an active basis by weight of pulp fiber). The suspension is gently agitated another 5 minutes to allow for adsorption of the anionic latex on the now cationic fiber surface. The suspension is then vacuum drained through the screen in the deckle box. The wet cellulosic web is passed three times through a drum dryer at 120° C. to produce a strong, soft, paper product reinforced with latex binder. This product, when produced continuously in long sheets, can be useful as an agricultural ground covering.

What is claimed is:

1. A polymer which is made by polymerizing a monomer mixture comprising:

A. from about 50 to about 98% by weight of a polyene having at least 6 carbon atoms and having the formula:

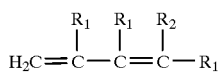

or

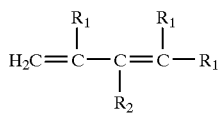

wherein each $R_1$ is independently H, halo, amino, cyano, carboxy, $C_1$–$C_4$ alkyl, $C_1$–$C_4$ alkoxy, $C_1$–$C_4$ ester, $C_6$–$C_{12}$ aryl, or $C_6$–$C_{12}$ heteroaryl; and $R_2$ is H, halo, amino, hydroxy, cyano, carboxy, $C_1$–$C_{16}$ alkyl, $C_1$–$C_4$ alkoxy, $C_1$–$C_4$ ester, $C_6$–$C_{12}$ aryl, $C_4$–$C_{12}$ heteroaryl or $C_2$–$C_{12}$ alkenyl;

B. from about 2 to about 70% by weight of a crosslinking agent having at least 2 activated double bonds; and C. up to about 25% by weight other compatible comonomers.

2. The polymer of claim 1 wherein said polyene has from 6 to 20 carbon atoms.

3. The polymer of claim 2 wherein said polyene is selected from the group consisting of 1,3-hexadiene, 1,3-heptadiene, 1,3-octadiene, 1,3-nonadiene, 1,3decadiene, 1,3-undecadiene, 1,3-dodecadiene, 2-methyl-1,3-hexadiene, 6-methyl-1,3-heptadiene, 7-methyl-1,3-octadiene, 1,3,7-octatriene, 1,3,9-decatriene, 1,3,6-octatriene, 2,3-dimethyl-1,3-butadiene, 2-amyl-1,3-butadiene, 2,6-dimethyl-1,3,7-octatriene, 2,7-dimethyl-1,3,7-octatriene, 2,6-dimethyl-1,3,6-octatriene, 2,7-dimethyl-1,3,6-octatriene, 7-methyl-3-methylene-1,6-octadiene, 2,6-dimethyl-1,5,7-octatriene, 1-methyl-2-vinyl-4,6-hepta-dieny-3,8-nonadienoate, 5-methyl-1,3,6-heptatriene, 2-ethyl-1,3-butadiene and mixtures thereof.

4. The polymer of claim 2 wherein said polyene has from 6 to 10 carbon atoms and has the formula:

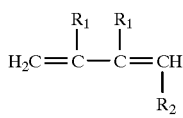

-continued or

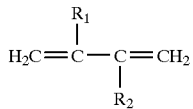

wherein each $R_1$ is independently H, $C_1$–$C_4$ alkyl, $C_1$–$C_4$ alkenyl, or $C_1$–$C_4$ alkoxy; and $R_2$ is H, $C_1$–$C_4$ alkyl, $C_1$–$C_4$ alkenyl, or $C_1$–$C_4$ alkoxy.

5. The polymer of claim 4 wherein said polyene is selected from the group consisting of 1,3-hexadiene, 1,3-octadiene, 2,3-dimethyl-1,3-butadiene, 2-ethyl-1,3-butadiene, 2-amyl-1,3-butadiene, 7-methyl-3-methylene-1,6-octadiene, 1,3,7-octatriene and mixtures thereof.

6. The polymer of claim 5 wherein said polyene is 1,3,7-octatriene.

7. The polymer of claim 1 wherein said crosslinking agent selected from the group consisting of divinylbenzenes, divinyltoluenes, divinylxylenes, divinylnaphthalenes divinylethylbenzenes, divinylphenanthrenes, trivinylbenzenes, divinylbiphenyles, divinyldiphenylmethanes, divinylbenzyls, divinylphenylethers, divinyldiphenylsulfides, divinylfurans, divinylsulfone, divinylsulfide, divinyldimethylsilane, diallyldimethyl ammonium chloride, 1,1'-divinylferrocene, 2-vinylbutadiene, and mixtures thereof.

8. The polymer of claim 1 wherein said crosslinking agent has the formula:

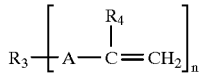

wherein each A is a linking group; $R_3$ is $C_1$–$C_{12}$ alkylene, $C_2$–$C_{12}$ alkenylene, $C_6$–$C_{12}$ arylene, $C_7$–$C_{18}$ arylalkylene, $C_4$–$C_{12}$ heteroarylene, $C_6$–$C_{18}$ heteroarylalkylene, $C_8$–$C_{18}$ arylalkenylene, or $C_8$–$C_{18}$ heteroarylalkenylene; $R_4$ is H, halo, carboxy, $C_1$–$C_4$ alkyl, $C_1C_4$ alkoxy, $C_1$–$C_4$ ester, $C_6$–$C_{12}$ aryl, or $C_4$–$C_{12}$ heteroaryl; n is at least 2.

9. The polymer of claim 8 wherein said linking group is selected from the group consisting of carboxy ester groups, amide groups, carbonate ester groups, sulfonate ester groups, phosphonate ester groups, carboxy anhydride groups, sulfonic anhydride groups, ether groups, and alkenyl groups.

10. The polymer of claim 9 wherein said linking group is selected from the group consisting of carboxy ester groups, amide groups and ether groups.

11. The polymer of claim 10 wherein said crosslinking agent is selected from the group consisting of ethylene glycol dimethacrylate, neopentyl glycol dimethacrylate, 1,3-butanediol dimethacrylate, diethylene glycol dimethacrylate, hydroquinone dimethacrylate, catechol dimethacrylate, resorcinol dimethacrylate, triethylene glycol dimethacrylate, polyethylene glycol dimethacrylate; trimethylolpropane trimethacrylate, pentaerythritol tetramethacrylate, 1,4-butanediol dimethacrylate, 1,6-hexanediol diacrylate, 1,4-butanediol diacrylate, tetramethylene diacrylate, trimethyol propane triacrylate, pentaerythritol tetraacrylate, N-methylolacrylamide, 1,2-ethylene bisacrylamide, 1,4-butane bisacrylamide, and mixtures thereof.

12. The polymer of claim 11 wherein said crosslinking agent is selected from the group consisting of acrylate and methacrylate esters having the formula:

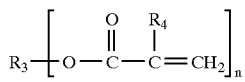

wherein $R_3$ is $C_2$–$C_6$ alkylene or oxyalkylene; $R_4$ is H or methyl; and n is 2 to 4.

13. The polymer of claim 12 wherein said crosslinking agent is selected from the group consisting of ethylene glycol dimethacrylate, diethylene glycol dimethacrylate, 1,6-hexanediol diacrylate, 2-butenediol dimethacrylate, ethylene glycol diacrylate, trimethylolpropane triacrylate and trimethacrylate, and mixtures thereof.

14. The polymer of claim 1 wherein said other compatible monomers are selected from the group consisting of chloroprene, tetrafluoroethylene, chlorotrifluoroethylene, hexafluoropropylene, styrene, o-methoxystyrene, p-methoxystyrene, m-methoxystyrene, o-methyl styrene, o-phenyl styrene, vinyl naphthalene, vinyl chloride, vinyl fluoride, vinylidene chloride, vinylidene fluoride, vinylidene bromide, acrylic acid, chloroacrylic acid, methacrylic acid, methyl acrylate, ethyl acrylate, butyl acrylate, n-octyl acrylate, 2ethylhexyl acrylate, methyl methacrylate, butyl methacrylate, acrylamide, N-methylacrylamide, N,N-dimethylacrylamide, N,N-dimethyl-methacrylamide, acrylonitrile, methacrylonitrile, maleic anhydride, dimethyl maleate, vinyl methyl ether, vinyl ethyl ether, vinyl isobutyl ether, methyl vinyl ketone, ethyl vinyl ketone, and isobutyl vinyl ketone; butadiene, isoprene, piperylene, cyclopentadiene, norbornadiene, dicyclopentadiene, vinylpyridine, N-vinylcarbazole, N-vinylpyrrolidine, acrolein, vinylferrocene, vinyltitanocene, methyl vinylsulfone, vinylpyridine, 2-vinylbutadiene, and mixtures thereof.

15. A polymeric foam which absorbs aqueous fluids, said polymeric foam comprising a hydrophilic, flexible, nonionic foam structure of interconnected open cells and which is made by polymerizing a water-in-oil emulsion having:
1) an oil phase comprising:
a) from about 65 to about 98% by weight of a monomer component comprising:
i) from about 30 to about 98% by weight of a polyene having at least 6 carbon atoms and having the formula:

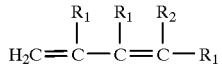

or

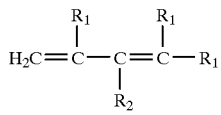

wherein $R_1$ are H, halo, amino, cyano, carboxy, $C_1$–$C_4$ alkyl, $C_1$–$C_4$ alkoxy, $C_1$–$C_4$ ester, $C_6$–$C_{12}$ aryl, $C_6$–$C_{12}$ heteroaryl, or mixtures thereof; $R_2$ are, H, halo, amino, hydroxy, cyano, carboxy, $C_1$–$C_{16}$ alkyl, $C_1$–$C_4$ alkoxy, $C_1$–$C_4$ ester, $C_6$–$C_{12}$ aryl, $C_4$–$C_{12}$ heteroaryl or $C_2$–$C_{12}$ alkenyl;
ii) from about 2 to about 70% by weight of a crosslinking agent having at least 2 activated double bonds;

iii) up to about 25% by weight other compatible comonomers;
b) from about 2 to about 35% by weight of an emulsifier component which is soluble in the oil phase and which forms a stable water-in-oil emulsion; and
2) a water phase comprising from about 0.2 to about 20% by weight of a water-soluble electrolyte,
3) a weight ratio of water phase to oil phase of from about 12:1 to about 100:1.

16. The foam of claim 15 wherein the weight ratio of water to oil phase is from about 20:1 to about 70:1.

17. The foam of claim 16 wherein the weight ratio of water to oil phase is from about 25:1 to about 50:1.

18. The foam of claim 17 wherein the oil phase comprises:
a) from about 80 to about 97% by weight of a monomer component comprising:
i) from about 60 to about 90% by weight of said polyene,
ii) from about 10 to about 40% by weight of said crosslinking agent;
iii) up to about 20% by weight of said comonomer; and
b) from about 3 to about 20% by weight of said emulsifier.

19. The foam of claim 18 in a collapsed state which, upon contact with said fluids, expands and absorbs said fluids, and wherein said foam structure has:
A) a specific surface area per foam volume of at least about 0.025 $m^2$/cc;
B) at least about 0.1% by weight of a toxicologically acceptable hygroscopic, hydrated salt incorporated therein;
C) in its collapsed state, an expansion pressure of about 30 kpa or less; and
D) in its expanded state, a density when saturated at 88° F. (31° C.) to its free absorbent capacity with synthetic urine having a surface tension of 65±5 dynes/cm of from about 10 to about 50% of its dry basis density in its collapsed state.

20. The foam of claim 15 wherein the oil phase further comprises an effective amount of a plasticizer selected from the group consisting of dioctyl azelate, dioctyl sebacate and dioctyl adipate.

21. A polymer which made by polymerizing a monomer mixture comprising:
A. from about 30 to about 98% by weight of a polyene having from 6 to 10 carbon atoms and having the formula:

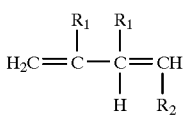

or

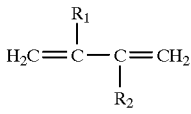

wherein $R_1$ is H, $C_1$–$C_4$ alkyl, $C_1$–$C_4$ alkenyl, or $C_1$–$C_4$ alkoxy; $R_2$ is H, $C_1$–$C_4$ alkyl, $C_1$–$C_4$ alkenyl or $C_1$–$C_4$ alkoxy;

B. from about 2 to about 70% by weight of a crosslinking agent having the formula:

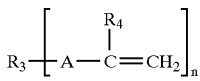

wherein each A is a cleavable linking group; $R_3$ is $C_1$–$C_{12}$ alkylene, $C_2$–$C_{12}$ alkenylene, $C_6$–$C_{12}$ arylene, $C_7$–$C_{18}$ arylalkylene, $C_4$–$C_{12}$ heteroarylene, $C_6$–$C_{18}$ heteroarylalkylene, $C_8$–$C_{18}$ arylalkenylene, or $C_8$–$C_{18}$ heteroarylalkenylene; $R_4$ is H, halo, carboxy, $C_1C_4$ alkyl, $C_1$–$C_4$ alkoxy, $C_1$–$C_4$ ester, $C_6$–$C_{12}$ aryl or $C_4$–$C_{12}$ heteroaryl; n is at least 2;

C. up to about 25% by weight a compatible comonomer selected from the group consisting of chloroprene, tetrafluoroethylene, chlorotrifluoroethylene, hexafluoropropylene, styrene, o-methoxystyrene, p-methoxystyrene, m-methoxystyrene, o-methyl styrene, o-phenyl styrene, vinyl naphthalene, vinyl chloride, vinyl fluoride, vinylidene chloride, vinylidene fluoride, vinylidene bromide, acrylic acid, chloroacrylic acid, methacrylic acid, methyl acrylate, ethyl acrylate, butyl acrylate, n-octyl acrylate, 2-ethylhexyl acrylate, methyl methacrylate, butyl methacrylate, acrylamide, N-methylacrylamide, N,N-dimethylacrylamide, N,N-dimethyl-methacrylamide, acrylonitrile, methacrylonitrile, maleic anhydride, dimethyl maleate, vinyl methyl ether, vinyl ethyl ether, vinyl isobutyl ether, methyl vinyl ketone, ethyl vinyl ketone, and isobutyl vinyl ketone; butadiene, isoprene, piperylene, cyclopentadiene, norbornadiene, dicyclopentadiene, vinylpyridine, N-vinylcarbazole, N-vinylpyrrolidine, acrolein, vinylferrocene, vinyltitanocene, methyl vinylsulfone, vinylpyridine, 2-vinylbutadiene, and mixtures thereof.

22. The polymer of claim 21 wherein said polyene is selected from the group consisting of 1,3-hexadiene, 1,3-octadiene, 2,3-dimethyl-1,3-butadiene, 2-ethyl-1,3-butadiene, 2-amyl-1,3-butadiene, 7-methyl-3-methylene-1,6-octadiene, 1,3,7-octatriene and mixtures thereof; and wherein said crosslinking agent is selected from the group consisting of ethylene glycol dimethacrylate, diethylene glycol dimethacrylate, 1,6-hexanediol diacrylate, 2-butenediol dimethacrylate, ethylene glycol diacrylate, trimethylolpropane triacrylate and trimethacrylate, and mixtures thereof.

23. The polymer of claim 22 wherein said polyene is 1,3,7-octatriene and wherein said crosslinking agent is ethylene glycol dimethacrylate.

24. A polymeric foam which absorbs aqueous body fluids, said polymeric foam comprising a hydrophilic, flexible, nonionic foam structure of interconnected open cells and which is made by polymerizing a water-in-oil emulsion having:

1) an oil phase comprising:
   a) from about 80 to about 97% by weight of a monomer component comprising:
      i) from about 60 to about 90% by weight of a polyene selected from the group consisting of 1,3-hexadiene, 1,3-octadiene, 2,3-dimethyl-1,3-butadiene, 2-ethyl-1,3-butadiene, 2-amyl-1,3-butadiene, 7-methyl-3-methylene-1,6-octadiene, 1,3,7-octatriene and mixtures thereof;
      ii) from about 10 to about 40% by weight of a crosslinking agent selected from the group consisting of ethylene glycol dimethacrylate, diethylene glycol dimethacrylate, 1,6-hexanediol diacrylate, 2-butenediol dimethacrylate, ethylene glycol diacrylate, trimethylolpropane triacrylate and trimethacrylate, and mixtures thereof;
      iii) up to about 20% by weight a compatible comonomer selected from the group consisting of chloroprene, tetrafluoroethylene, chlorotrifluoroethylene, hexafluoropropylene, styrene, o-methoxystyrene, p-methoxystyrene, m-methoxystyrene, o-methyl styrene, o-phenyl styrene, vinyl naphthalene, vinyl chloride, vinyl fluoride, vinylidene chloride, vinylidene fluoride, vinylidene bromide, acrylic acid, chloroacrylic acid, methacrylic acid, methyl acrylate, ethyl acrylate, butyl acrylate, n-octyl acrylate, 2-ethylhexyl acrylate, methyl methacrylate, butyl methacrylate, acrylamide, N-methylacrylamide, N,N-dimethylacrylamide, N,N-dimethylmethacrylamide, acrylonitrile, methacrylonitrile, maleic anhydride, dimethyl maleate, vinyl methyl ether, vinyl ethyl ether, vinyl isobutyl ether, methyl vinyl ketone, ethyl vinyl ketone, and isobutyl vinyl ketone; butadiene, isoprene, piperylene, cyclopentadiene, norbornadiene, dicyclopentadiene, vinylpyridine, N-vinylcarbazole, N-vinylpyrrolidine, acrolein, vinylferrocene, vinyltitanocene, methyl vinylsulfone, vinylpyridine, 2-vinylbutadiene, and mixtures thereof;

b) from about 3 to about 25% by weight of an emulsifier component which is soluble in the oil phase and which forms a stable water-in-oil emulsion; and 2) a water phase comprising from about 0.2 to about 20% by weight of a water-soluble electrolyte;

3) a weight ratio of water phase to oil phase of from about 25:1 to about 50:1.

25. The foam of claim 24 in a collapsed state which, upon contact with said fluids, expands and absorbs said fluids, and wherein said foam structure has:

A) a specific surface area per foam volume of at least about 0.025 m²/cc;

B) at least about 0.1% by weight of a toxicologically acceptable hygroscopic, hydrated salt incorporated therein;

C) in its collapsed state, an expansion pressure of about 30 kPa or less; and

D) in its expanded state, a density of from about 10 to about 50% of its dry basis density in its collapsed state.

26. The foam of claim 24 wherein the oil phase further comprises an effective amount of a plasticizer selected from the group consisting of dioctyl azelate, dioctyl sebacate and dioctyl adipate.

27. A process for producing a crosslinked polymer comprising polymerizing monomer component comprising from about 30 to about 98% by weight of a polyene having at least 6 carbon atoms and having the formula:

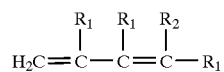

or

-continued

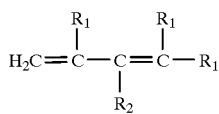

wherein $R_1$ are H, halo, amino, cyano, carboxy, $C_1$–$C_4$ alkyl, $C_1$–$C_4$ alkoxy, $C_1$–$C_4$ ester, $C_6$–$C_{12}$ aryl, $C_6$–$C_{12}$ heteroaryl, or mixtures thereof; $R_2$ is H, halo, amino, hydroxy, cyano, carboxy, $C_1$–$C_{16}$alkyl, $C_1$–$C_4$ alkoxy, $C_1$–$C_4$ ester, $C_6$–$C_{12}$ aryl, $C_4C_{12}$ heteroaryl or $C_2$–$C_{12}$ alkenyl;

from about 2 to about 70% by weight of a crosslinking agent having the formula:

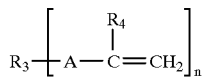

wherein A is a linking group; $R_3$ is $C_1$–$C_{12}$ alkylene, $C_2$–$C_{12}$ alkenylene, $C_6$–$C_{12}$ arylene, $C_7$–$C_{18}$ arylalkylene, $C_4$–$C_{12}$ heteroarylene, $C_6$–$C_{18}$ heteroarylalkylene, $C_8$–$C_{18}$ arylalkenylene, or $C_8$–$C_{18}$ heteroarylalkenylene; $R_4$ is H, halo, carboxy, $C_1$–$C_4$ alkyl, $C_1$–$C_4$ alkoxy, $C_1$–$C_4$ ester, $C_6$–$C_{12}$ aryl or $C_4$–$C_{12}$ heteroaryl; n is at least 2; and optionally up to about 25% by weight other compatible comonomers, in the presence of a polymerization initiator and an antioxidant.

28. The process of claim 27 wherein the antioxidant is selected from the group consisting of hindered amine light stabilizers and hindered phenolic stabilizers.

* * * * *

UNITED STATES PATENT AND TRADEMARK OFFICE
CERTIFICATE OF CORRECTION

PATENT NO. : 5,922,780
DATED : July 13, 1999
INVENTOR(S) : John C. Dyer et al.

It is certified that error appears in the above-identified patent and that said Letters Patent is hereby corrected as shown below:

Column 5,
Line 16, "divinyidiphenylmethanes" should read -- divinyldiphenylmethanes --.
Line 18, "divinidimethylsilane" should read -- divinyldimethylsilane --.

Column 21,
Line 40, "filly" should read -- fully --.

Signed and Sealed this

Ninth Day of April, 2002

JAMES E. ROGAN
Director of the United States Patent and Trademark Office

Attest:

Attesting Officer